United States Patent [19]

Dellaria et al.

[11] Patent Number: 5,484,786
[45] Date of Patent: Jan. 16, 1996

[54] PYRAN-4-YLMETHYL SUBSTITUTED ARYLALKYLARYL-, ARYLALKENYLYLARYL-, AND ARYLALKYNYLARYLUREA INHIBITORS OF 5-LIPOXYGENASE

[75] Inventors: Joseph F. Dellaria, Lindenhurst; Anwer Basha, Lake Forest; Lawrence A. Black, Vernon Hills; Linda J. Chernesky, Arlington Heights; Wendy Lee, Chicago, all of Ill.

[73] Assignee: Abbott Laboratories, Abbott Park, Ill.

[21] Appl. No.: 111,090

[22] Filed: Aug. 24, 1993

[51] Int. Cl.⁶ .................. A61K 31/35; A61K 31/495; C07D 315/00; C07D 239/04
[52] U.S. Cl. .................. 514/256; 514/392; 514/454; 544/316; 548/311.1; 549/426
[58] Field of Search .................. 549/426; 514/459, 514/256, 392; 544/316; 548/311.1

[56] References Cited

PUBLICATIONS

Chemical Abstract, vol. 79 No. 105085, Carr et al. 1979, "Antihestamine piperidine derivatives".

*Primary Examiner*—C. Warren Ivy
*Assistant Examiner*—Raymond Covington
*Attorney, Agent, or Firm*—Jerry F. Janssen

[57] ABSTRACT

Compounds of structure

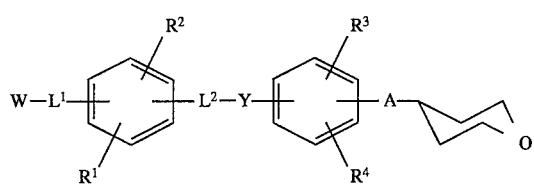

where W is selected from

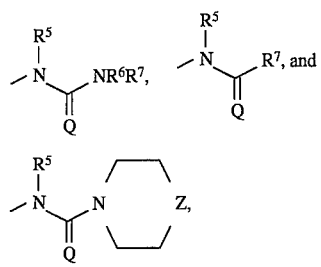

where Q is oxygen or sulfur, $R^5$ and $R^6$ are independently selected from hydrogen and alkyl, or $R^5$ and $R^6$, together with the nitrogen atoms to which they are attached, define a radical of formula

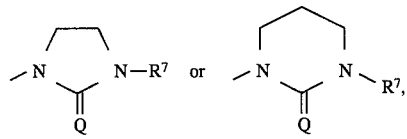

$L^1$ and $L^2$ are independently selected from a valence bond, alkylene, propenylene, and propynylene, $R^1$, $R^2$, $R^3$, and $R^4$ are independently selected from alkyl, alkoxy, haloalkyl, halogen, cyano, amino, alkoxycarbonyl, and dialkylaminocarbonyl, Y is oxygen, $>NR^9$ where $R^9$ is hydrogen or alkyl, or

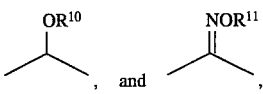

where n=0, 1, or 2, and A is selected from $$\overset{OR^{10}}{\underset{}{\bigwedge}}, \text{ and } \overset{NOR^{11}}{\underset{}{\bigwedge}},$$

inhibit the biosynthesis of leukotrienes. These compounds are useful in the treatment or amelioration of allergic and inflammatory disease states.

5 Claims, No Drawings 5,484,786

PYRAN-4-YLMETHYL SUBSTITUTED ARYLALKYLARYL-, ARYLALKENYLYLARYL-, AND ARYLALKYNYLARYLUREA INHIBITORS OF 5-LIPOXYGENASE

TECHNICAL FIELD

This invention relates to compounds having biological activity to inhibit lipoxygenase enzymes, to pharmaceutical compositions comprising these compounds, and to a medical method of treatment. More particularly, this invention concerns certain pyran-4-ylmethyl substituted arylalkylaryl-, arylalkenylaryl-, and arylalkynylarylurea compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxytrans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain triether compounds which inhibit lipoxygenase enzyme activity and are useful in the treatment of allergic and inflammatory disease states in which leukotrienes play a role.

The compounds of this invention and the pharmaceutically acceptable salts thereof have the structure

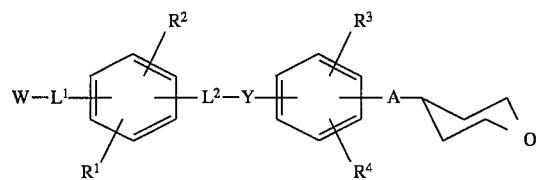

wherein W is selected from the group consisting of

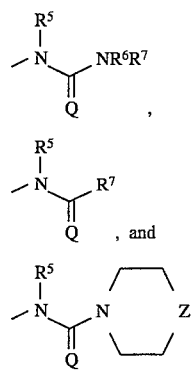

wherein Q is oxygen or sulfur, $R^5$ and $R^6$ are independently selected from the group consisting of hydrogen or alkyl of one to four carbon atoms, provided that when $L^1$ is a valence bond, $R^5$ is alkyl of one to four carbon atoms, or $R^5$ and $R^6$, together with the nitrogen atoms to which they are attached, define a radical of formula

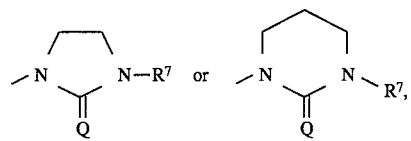

$R^7$ is selected from the group consisting of hydrogen; alkyl of one to four carbon atoms; haloalkyl of one to four carbon atoms; cyanoalkyl of one to four carbon atoms; phenyl, optionally substituted with alkyl of one to four carbon atoms, alkoxy of one to four carbon atoms, haloalkyl, or halogen; hydroxyalkyl of from one to four carbon atoms; aminoalkyl of from one to four carbon atoms; carboxyalkyl of from one to four carbon atoms; (alkoxycarbonyl)alkyl where the alkyl and alkoxy portions each are of one to four carbon atoms; (alkylaminocarbonyl)alkyl, where the alkyl and aminoalkyl portions each are of one to four carbon atoms; and Z is —$CH_2$—, oxygen, sulfur, or —$NR^8$ wherein $R^8$ is hydrogen or alkyl of one to four carbon atoms.

$L^1$ is a valence bond or is selected from alkylene of one to three carbon atoms, propenylene, and propynylene.

$R^1$, $R^2$, $R^3$, and $R^4$ are independently selected from the group consisting of alkyl of one to four carbon atoms, alkoxy of one to four carbon atoms, haloalkyl, halogen, cyano, amino, alkoxycarbonyl of one to four carbon atoms, and dialkylaminocarbonyl where the alkyl portions are each of one to four carbon atoms.

$L^2$ is a valence bond or is selected from alkylene of one to three carbon atoms, propenylene, and propynylene.

Y is selected from the group consisting of oxygen, >$NR^9$, where $R^9$ is hydrogen or alkyl of one to four carbon atoms, and

where n=0, 1, or 2.

A is selected from the group consisting of

 (a)

wherein $R^{10}$ is alkyl of one to four carbon atoms,

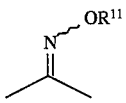 (b)

wherein $R^{110}$ is hydrogen or alkyl of one to four carbon atoms.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the stucture —NHR' wherein R' is alkyl as previously defined. Example of alkylamino include methylamino, ethylamino, iso-propylamino, and the like.

The term "alkylaminocarbonyl" refers to an alkylamino group, as previously defined, attached to the parent molecular moiety through a carbonyl group. Examples of alkylaminocarbonyl include methylaminocarbonyl, ethylaminocarbonyl, iso-propylaminocarbonyl, and the like.

The term "alkanoyl" refers to an alkyl group, as defined above, attached to the parent molecular moiety through a carbonyl group. Alkanoyl groups are exemplified by formyl, acetyl, butanoyl, and the like.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxycarbonyl" represents an ester group; i.e. an alkoxy group attached to the parent molecular moiety through a carbonyl group. Representative alkoxycarbonyl groups include methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight branched chain saturated hydrocarbon by the removal of two hydrogen atoms, for example methylene, 1,2-ethylene, 1,1-ethylene, 1,3-propylene, 2,2-dimethylpropylene, and the like.

The term "aminoalkyl" denotes an —$NH_2$ group attached to the parent molecular moiety through an alkylene group. Representative aminoalkyl groups include 2-amino-1-ethylene, 3-amino-1-propylene, 2-amino-1-propylene, and the like.

The term "carboxyalkyl" denotes a —$CO_2H$ group attached to the parent molecular moiety through an alkylene group. Representative carboxyalkyl groups include, 1-carboxyethyl, 2-carboxyethyl, 1-carboxypropyl, and the like.

The term "(alkoxycarbonyl)alkyl" denotes an alkoxycarbonyl group, as defined above, attached to the parent molecular moiety through an alkylene group. Representative (alkoxycarbonyl)alkyl groups include ethoxycarbonylmethyl, ethoxycarbonylethyl, methoxycarbonylpropyl, and the like.

The term "(alkylaminocarbonyl)alkyl" denotes an alkylaminocarbonyl group, as defined above, attached to the parent molecular moiety through an alkylene group. Examples of (alkylaminocarbonyl)alkyl groups include methylaminocarbonylmethyl, methylaminocarbonylpropyl, isopropylaminocarbonylmethyl, and the like.

The term "alkenylene" denotes a divalent group derived from a straight or branched chain hydrocarbon containing at least one carbon-carbon double bond. Examples of alkenylene include —CH=CH—, —$CH_2$CH=CH—, —C($CH_3$)=CH—, —$CH_2$CH=CH$CH_2$—, and the like.

In one preferred embodiment, the compounds of this invention have the structure

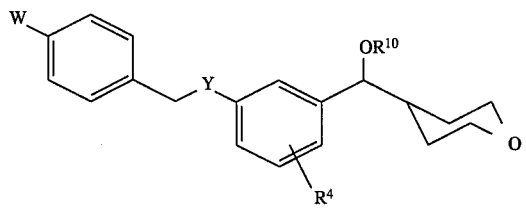

wherein W, Y, $R^4$, and A are as defined above.

Examples of compounds of this embodiment include, but are not limited to:

4-[(3-(4-   (N-acetyl-N-methylamino)benzyloxy)-5-fluorophenyl)methoxymethyl]-tetrahydropyran;

4-[(3-(4-(N-acetyl-N-methylamino)benzyloxy)phenyl) methoxymethyl]-tetrahydropyran;

4-[3-(4-(N',   N'-dimethylaminocarbonyl-N-methylamino)benzyloxy)-5-fluorophenyl)methoxymethyl]tetrahydropyran;

4-[3-(4-(N',   N'_dimethylaminocarbonyl-N-methylamino)benzyloxy)phenyl)-methoxymethyl]tetrahydropyran;

4-[3-(4-(N', N'-dimethylaminocarbonyl-N-methylamino)benzylthio)phenyl)-methoxymethyl]tetrahydropyran;

4-[3-(4-(N-acetyl-N-methylamino)benzylthio)phenyl)methoxymethyl]-tetrahydropyran;

4-[(3-(4-(N-acetyl-N-methylamino)benzylthio)-5-fluorophenyl)methoxy-methyl]tetrahydropyran;

4-[(3-(4-(N-thioacetyl-N-methylamino)benzylthio)-5-fluorophenyl)methoxy-methyl]tetrahydropyran;

4-[(3-(4-(N', N'-dimethylaminocarbony-N-methylamino)benzyl-N-methylamino)phenyl)oximinomethyl]tetrahydropyran, and 4-[(3-(4-(N-acetyl-N-methylamino)benzyl-N-methylamino)phenyl)-oximinomethyl]tetrahydropyran.

In another preferred embodiment, the compounds of this invention have the structure wherein W, n, $R^4$, and $R^{10}$ are as defined above.

Examples of compounds of this embodiment include, but are not limited to:

E and Z-4-[(3-(4-(N-acetyl-N-methylamino)phenylthio)phenyl)oximinomethyl]tetrahydropyran;

E and Z-O-Methyl-4-[(3-(4-(N-acetyl-N-methylamino)phenylthio)phenyl)-oximinomethyl]tetrahydropyran;

E and Z-O-Methyl-4-[(3-(4-(N-acetyl-N-methylamino)phenylsulfinyl)phenyl)-oximinomethyl]tetrahydropyran;

E- and Z-O-Methyl-4-[(3-(4-(n-acetyl-N-methylamino)phenylsulfonyl)-phenyl)oximinomethyl]tetrahydropyran;

E- and Z-O-Methyl-4-[(3-(4-(N', N'-dimethylaminocarbonyl-N-methylamino)-phenylthio)phenyl)oximinomethyl]

E- and Z-O-Methyl-4-[(3-(4-(N', N'-dimethylaminocarbonyl-N-methylamino)phenylsulfinyl)phenyl)oximinomethyl]tetrahydropyran; and E- and Z-O-Methyl-4[(3-(4(N', N'-dimethylaminocarbonyl-N-methylamino)phenylsulfonyl)phenyl)oximinomethyl] tetrahydropyran, In the most preferred embodiment, the compounds of this invention have the structure wherein W, Y, $R^4$, and $R^{11}$ are as defined above.

Examples of compounds of this embodiment include, but are not limited to:

E- and Z-O-Methyl-4-[(3-(4-(N-acetyl-N-methylamino)benzyloxy)-5-fluorophenyl)oximinomethyl]tetrahydropyran;

E- and Z-4-[(3-(4-(N-acetyl-N-methylamino)benzyloxy)5-fluorophenyl)oximinomethyl]tetrahydropyran;

E-and Z-O-Methyl-4-[(3-(4-(N-acetyl-N-methylamino)benzyloxy)phenyl)-oximinomethyl]tetrahydropyran;

E- and Z-4-[(3-(4-(N-acetyl-N-methylamino)benzyloxy)phenyl)-oximinomethyl]tetrahydropyran;

E- and Z-O-Methyl-4-[(3-(4-(N', N'-dimethylminocarbonyl-N-methylamino)-benzyloxy)phenyl)oximinomethyl]tetrahydropyran;

E- and Z-4-[(3-(4(N', N'-dimethylminocarbonyl-N-methylamino)benzyloxy)-5-fluorophenyl)oximinomethyl]tetrahydropyran;

E- and Z-O-Methyl-4-[(3-(4-(N', N'-dimethylaminocarbonyl-N-methylamino)-benzylamino)phenyl)oximinomethyl]tetrahydropyran;

E- and Z-4-[(3-(4-(N',N'-dimethylaminocarbonyl-N-methylamino)benzyloxy)phen-1-yl)oximinomethyl]tetrahydropyran;

E- and Z-O-Methyl-4-[(3-(4-(N',N'-dimethylaminocarbonyl-N-methylamino) -benzylamino)phenyl)oximinomethyl]tetrahydropyran;

E- and Z-O-Methyl-4-[(3-(4-(N-acetyl-N-methylamino)benzylamino)phenyl)-oximinomethyl]tetrahydropyran;

E- and Z-O-Methyl-4-[(3-(4-(N', N'-dimethylaminocarbonyl-N-methylamino)benzylthio)-5-fluorophenyl)oximinomethyl]tetrahydropyran;

E- and Z-O-Methyl-4-[(3-(4-(N', N'-dimethylaminocarbonyl-N-methylamino)benzylthio)phenyl)oximinomethyl] tetrahydropyran;

E- and Z-4-[(3-(4-(N', N'-dimethylaminocarbonyl-N-methylamino)benxylthio)phenyl)oximiminomethyl]tetrahydropyran;

E- and Z-O-Methyl-4-[(3-(4-(N-acetyl-N-methylamino)benzylthio)phenyl)oximinomethyl]tetrahydropyran;

E- and Z-4-[(3-(4-(N-acetyl-N-methylamino)benzylthio)phenyl)-oximinomethyl]tetrahydropyran;

E- and Z-O-Methyl-4-[(3-(4(N-acetyl-N-methylamino)benxylthio)-5-fluorophenyl)oximinomethyl]tetrahydropyran;

E- and Z-4-[(3-(4-(N-acetyl-N-methylamino)benzylthio)-5-fluorophenyl)oximinomethyl]tetrahydropyran;

E- and Z-O-Methyl-4-[(3-(4-(N-thioacetyl-N-methylamino)benxylthio)-5-fluorophenyl)oximinomethyl]tetrahydropyran;

E- and Z-O-Methyl-4[(3-(4-(N', N'-dimethylaminothiocarbonyl-N-methylamino)benzylthio)phenyl)oximinomethyl]tetrahydropyran;

E- and Z-O-Methyl-4-[(3-(4-N-aminocarbonyul-N-methylamino)benzyloxy)-5-fluorophenyl)oximinomethyl]tetrahydropyran;

E- and Z-O-Methyl-4-[(3-(4-(N'-methylaminocarbonyl-N-methylamino)benzyloxy)-5-fluorophenyl)oximinomethyl]tetrahydropyran;

E- and Z-O-Methyl-4-[(3-(4-N-(piperidin-1-ylcarbonyl)-N-methylamino)benzyloxy)-5-fluorophenyl)oximinomethyl]tetrahydropyran;

E- and Z-O-Methyl-4[(3-(4-(N-(piperidin-1-ylcarbonyl)amino)benzyloxy)-5-fluorophenyl)oximinomethyl]tetrahydropyran;

E- and Z-O-Methyl-4-[(3-(4-((4-morpholinocarbonyl)-N-methylamino)benzyloxy)-5-fluorophenyl)oximinomethyl]tetrahydropyran;

E- and Z-O-Methyl-4-[(3-(4((4-thiomorpholinocarbonyl)-N-methylamino)benzyloxy)-5-fluorophenyl)oximinomethyl]tetrahydropyran;

E- and Z-O-Methyl-4[(3(4-(N-(4-methylpiperazin-1-ylcarbonyl)-N-methylamino)benzyloxy)-5-fluorophenyl)oximinomethyl]tetrahydropyran;

E- and Z-O-Methyl-4-[(3-(4-((N'-(3-bromoprop-1-yl)aminocarbonyl)-N-methylamino)benzyloxy)-5-fluorophenyl)oximinomethyl]tetrahydropyran;

E- and Z-O-Methyl-4-[(3-(4-((N'(3-aminoprop-1-yl)aminocarbonyl)-N-methylamino)benzyloxy)-5-fluorophenyl)oximinomethyl]tetrahydropyran;

E- and Z-O-Methyl-4-[(3-(4-((N'-(3-hyroxyprop-1-yl)ami-nocarbonyl)-N-methylamino)benzyloxy)-5fluorophenyl)oximinomethyl]tetrahydropyran;

E- and Z-O-Methyl-4-[(3-(4-((N'-(3-ethoxycarbonylprop-1-yl)aminocarbonyl)-N-methylamino)benzyloxy)-5-fluorophenyl)oximinomethyl]tetrahydropyran;

E- and Z-O-Methyl-4-[(3-(4-((N'-(3-carboxyprop-1-yl)aminocarbonyl)-N-methylamino)benzyloxy)-5-fluorophenyl)oximinomethyl]tetrahydropyran;

E- and Z-O-Methyl-4-[(3-(4-((N-(4-hydroxybut-1-yl)aminocarbonyl)-N-methylamino)benzyloxy)-5-fluorophenyl)oximinomethyl]tetrahydropyran;

E- and Z-O-Methyl-4-[3-(4((N-(4-cyanobut-1-yl)aminocarbonyl)-N-methylamino)benzyloxy)-5-fluorophenyl)oximinomethyl]tetrahydropyran;

E- and Z-O-Methyl-4-[(3-(4-((N-(4-aminobut-1-yl)aminocarbonyl)-N-methylamino)benzyloxy)-5-fluorophenyl)oximinomethyl]tetrahydropyran;

E-and Z-O-Methyl-4-[(3-(4-((N-(3-carboxyprop-1-yl)aminocarbonyl)-N-methylamino)benzyloxy)-5-fluorophenyl)oximinomethyl]tetrahydropyran;

E- and Z-O-Methyl-4-[(3-(4-((N-(3-(N'-methylaminocarbonyl)prop-1-yl)aminocarbonyl)-N-methylamino)benzyloxy)-5-fluorophenyl)oximinomethyl]tetrahydropyran;

E- and Z-O-Methyl-4-[(3-(4-(N',N'-dimethylamincarbonyl-N-methylamino)benzylamino)phenyl)oximinomethyl]tetrahydropyran; and E- and Z-O-Methyl-4-[(3-(4-(N-acetyl-N-methylamino)benzylamino)phenyl)-oximinomethyl]tetrahydropyran.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min 37° C. followed by calcium ionophore A23187 challenge (final concentration of 8.3 µM) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis as illustrated in Table 1.

TABLE 1

In Vitro Inhibitory Potencies of Compounds of this Invention Against 5-Lipoxygenase from Stimulated $LTB_4$ Formation in Human Whole Blood

| Example | $IC_{50}$ ($10^{-6}$ M) |
| --- | --- |
| 1 | 100% @ 1.56 µM |
| 5 | 100% @ 0.78 µM |
| 43 | 12% @ 3.13 µM |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as will as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of this Invention

The compounds of this invention can be prepared by a variety of synthetic routes. Representative procedures are outlined as follows. It should be understood that $L^1$, $R^5$, $R^6$, $R^7$, $R^8$, $R^9$, $R^{10}$, and W as used herein correspond to the groups identified above.

A general route to the compounds of this invention is shown in Scheme 1. Alkylation of 1 by treatment with NaH and 2 provides ketone 3. Methoxymethyl derivative 4 is obtained by reduction of 3 with $NaBH_4$ and alkylation with $R^9X$. Oxime derivative 5 is prepared by reaction of 3 with the desired hydroxylamine hydrochloride in the presence of base.

Scheme 1

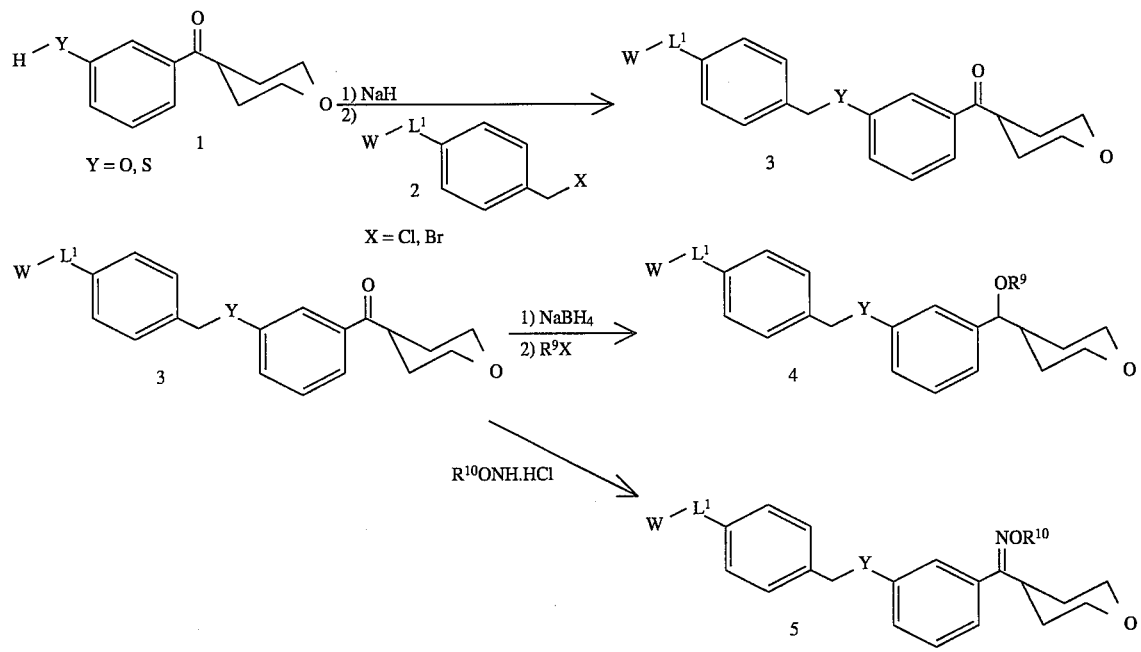

The preparation of compounds where $R^6$ is alkyl is shown in Scheme 2.4-aminobenyzl alcohol is reacted tert-butyldimethylsilyl choloride to form 6, which is then diacylated by treatment sodium acetate and acetic anhydride according to the method of Corley, R. S. and Blout, E. R., *J. Am. Chem. Soc.* 1947, 69, 755, 761 to form 7. Conversion of 7 to the bromide is accomplished as described by Aizupurua, J. M., Cossio, F. R., and Paloma, C., *J. Org. Chem.* 1986, 51, 4941. Arylalkyl-aryl ether 9 is then prepared from bromide 8 as described in scheme 1. Treatment of 9 with one equivalent of LiOH results in removal of one acetyl group to form 10, which is then alkylated by treatment with NaH and the desired alkyl halide to form 11. The second acyl group is removed by treatment of 11 with KOH to form key intermediate 12, which can be reacted with trimethylsilylisocyanate to form 13, or deprotonated with lithium bis(trimethylsilyl)amide and acylated with the desired carbamyl chloride to form 14.

Scheme 2

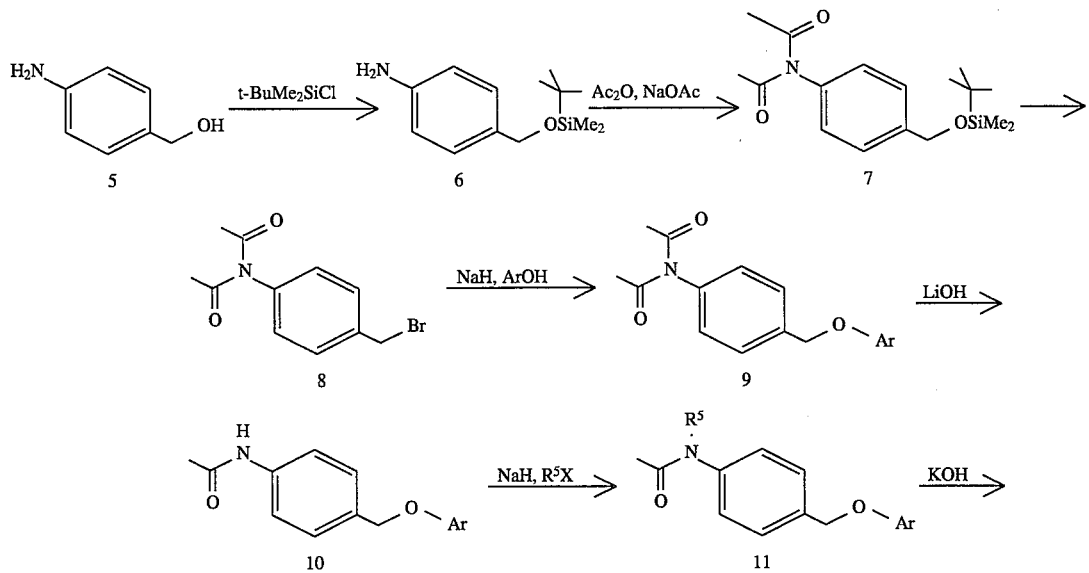

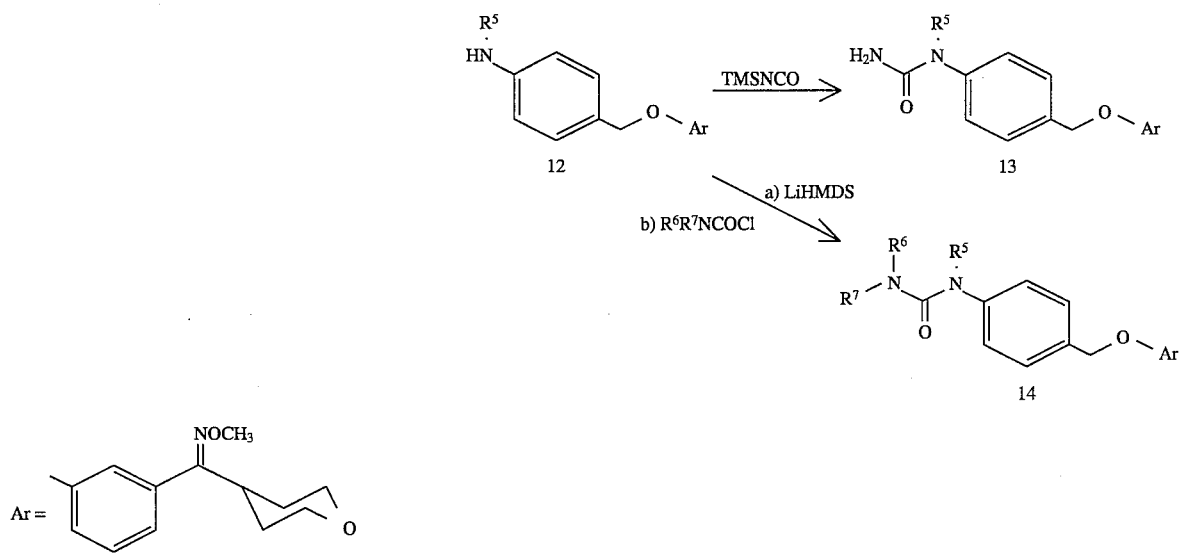

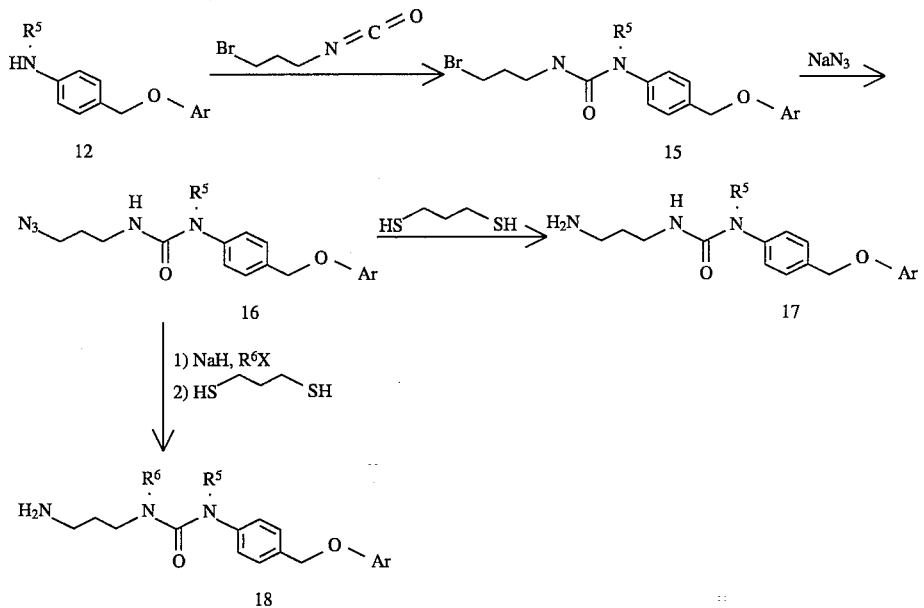

The preparation of the compounds of this invention where $R^8$ is haloalkyl, or aminoalkyl is shown in Scheme 3. Amine 12, prepared as in scheme 3, is treated with the desired haloalkylisocyanate to form haloalkyl derivative 15. Conversion of 15 to azide 16, followed by reduction of the azide with 1,3-propanedithiol provides aminoalkyl derivative 17. Compounds in which $R^6$ is alkyl are prepared by alkylation of 16 followed by reduction with propanedithiol as described above.

The preparation of the compounds of this invention where $R^8$ is hydroxyalkyl, carboxyalkyl, (alkoxycarbonyl)alkyl, or (alkylaminocarbonyl)alkyl, is shown in Scheme 4. Amine 12 is treated with an alkoxycarbonylalkylisocyanate to provide the alkoxycarbonylalkyl derivative 19, which is alkylated by treatment with NaH and $R^6X$. Hydrolysis of ester 20 provides (alkoxycarbonyl)alkyl derivative 21. Reduction of 20 with lithium borohydride or 21 with $BH_3$ provides the hydroxyalkyl compound 22. Ester 19 is hydrolyzed or reduced as described above to prepare the derivatives wherein $R^6$ is H. The (alkylaminocarbonyl)alkyl derivatives are prepared from esters 19 and 20, or acids 21 and 23 by standard synthetic methods.

Scheme 4

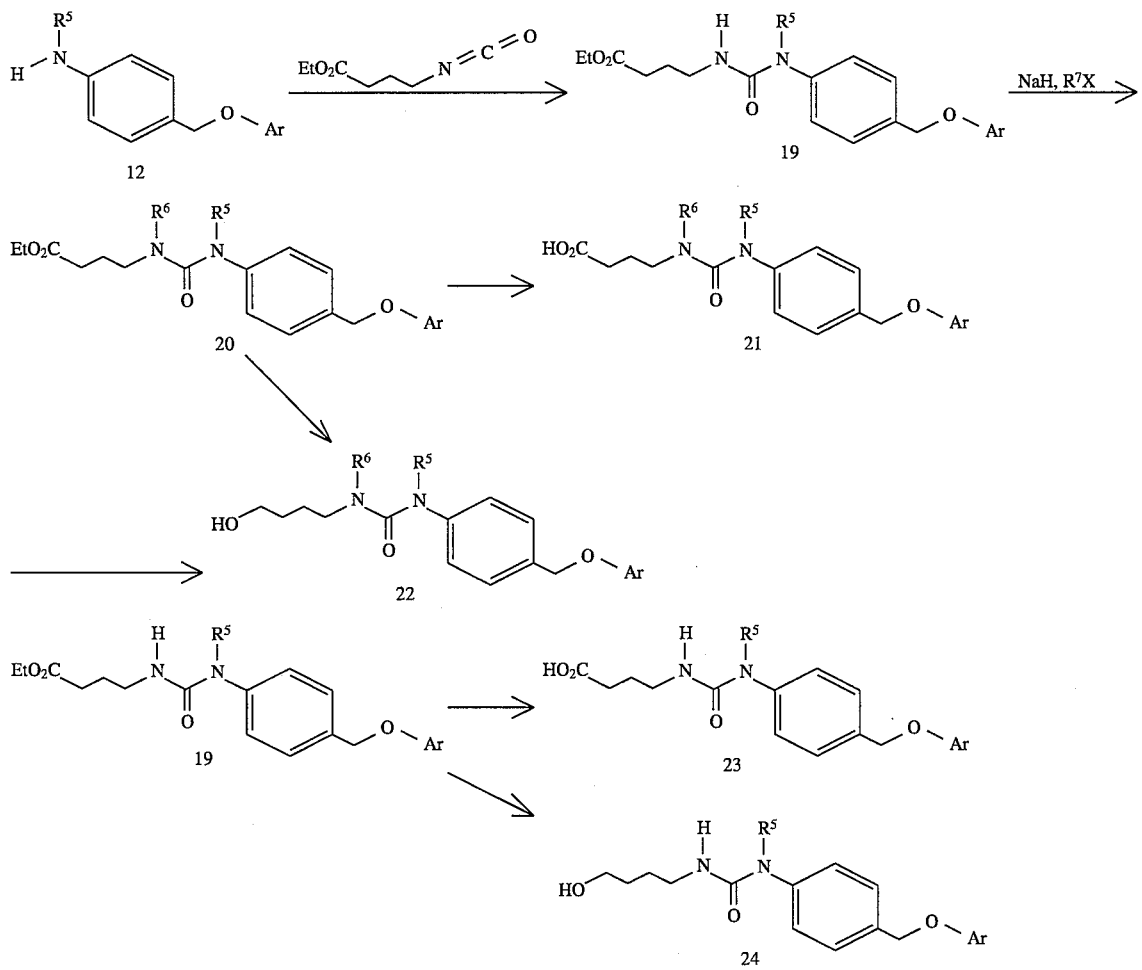

The preparation of N-acyl compounds is shown in Scheme 5. Methyl 4-(N-methylamino)benzoate (25) is acylated with allyl chloroformate for form 26. Benzyl chloride 27 is prepared by reduction of the ester with lithium triethylborohydride and treatment of the resulting benzyl alcohol with $PCl_3$. Arylalkyl-aryl ether 28 is then prepared from chloride 27 as described in Scheme 1. Carbamate 28 is hydrolyzed according to the method of Corey, E. J., and Suggs, J. W., *J. Org. Chem.*, 1973,38, 3223, and the resulting amine is acylated by treatment with lithium hexamethyldisylazide and 4-pentenoyl chloride to form 29. Reaction of 29 with borane-pyridine forms alcohol 30, which is oxidized to 31 by treatment with Jone's reagent. Amide 32 is prepared by the DCC-catalyzed coupling of 31 and $R^6R^7NH$.

Alcohol 30 is converted to primary iodide 33 treatment with methanesulfonyl chloride and NaI. Displacement of iodide with NaCN produces alkylcyano derivative 34. Displacement of iodide with $NaN_3$, followed by reduction of the azide with 1,3-propanedithiol forms alkylamine 35.

The preparation of the arylpropynyl-,arylpropenyl-,and arylpropyl-aryl ethers is shown in Scheme 6. 4-iodoaniline is converted to urea 36 by acylation with dimethylcarbamyl chloride, followed by alkylation with NaH and MeI. Coupling of 36 with propargyl alcohol provides propynol 37 which is converted to chloride 38 by treatment with phosphorus trichloride. The desired arylpropynyl-aryl ether 39 is prepared as described in scheme 1.

Treatment of alkynol 37 with Red-Al (sodium bis(2-methoxyethoxy) aluminum hydride) provides trans allylic alcohol 40, which is then coupled with 2 in the presence of triphenylphosphine and diethylaminodicarboxylate. Catalytic hydrogenation of 41 provides saturated compound 42.

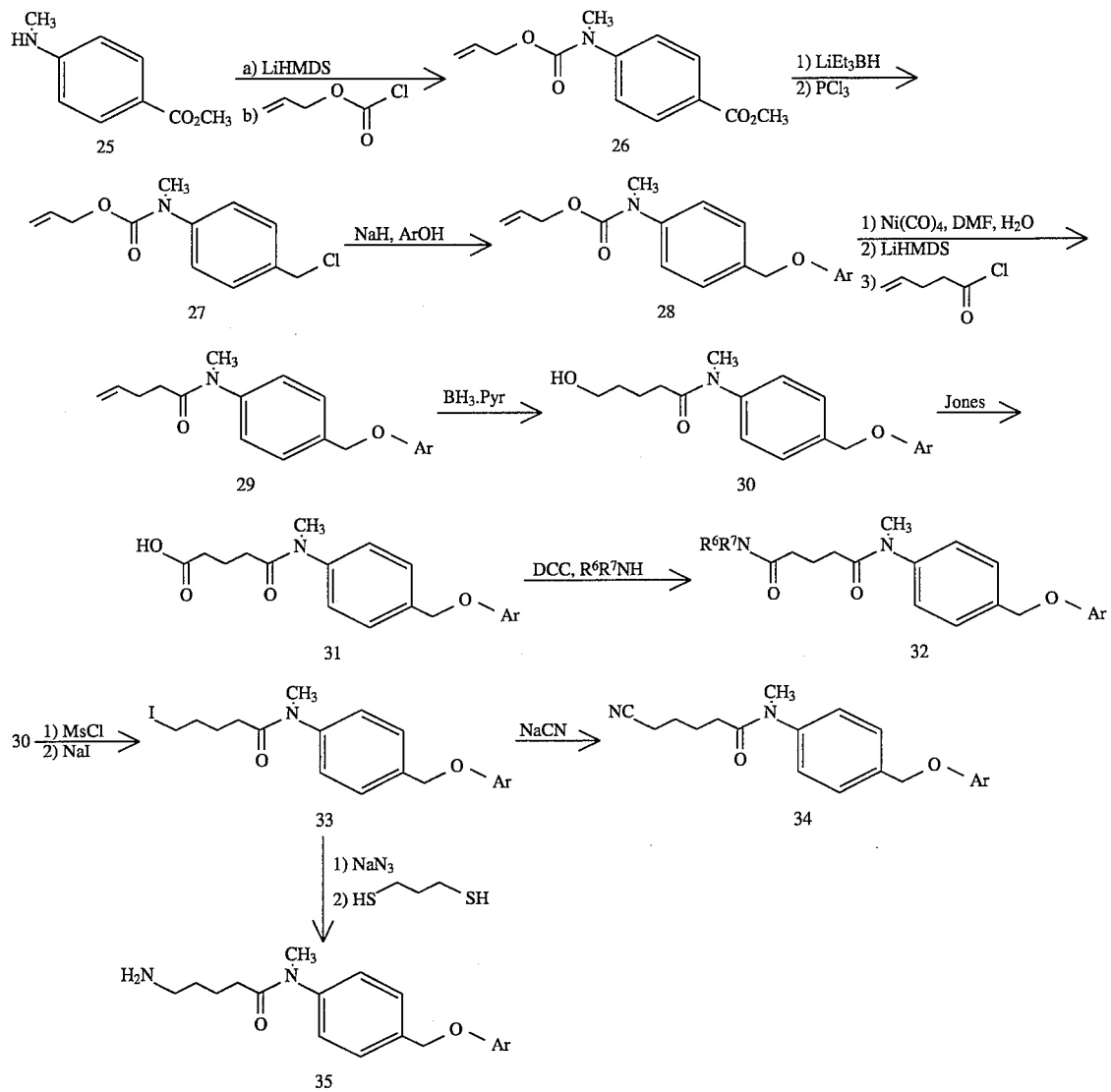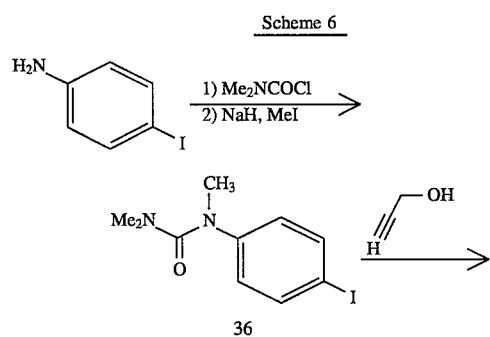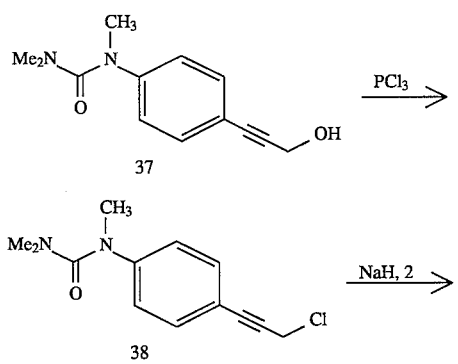

-continued
Scheme 6

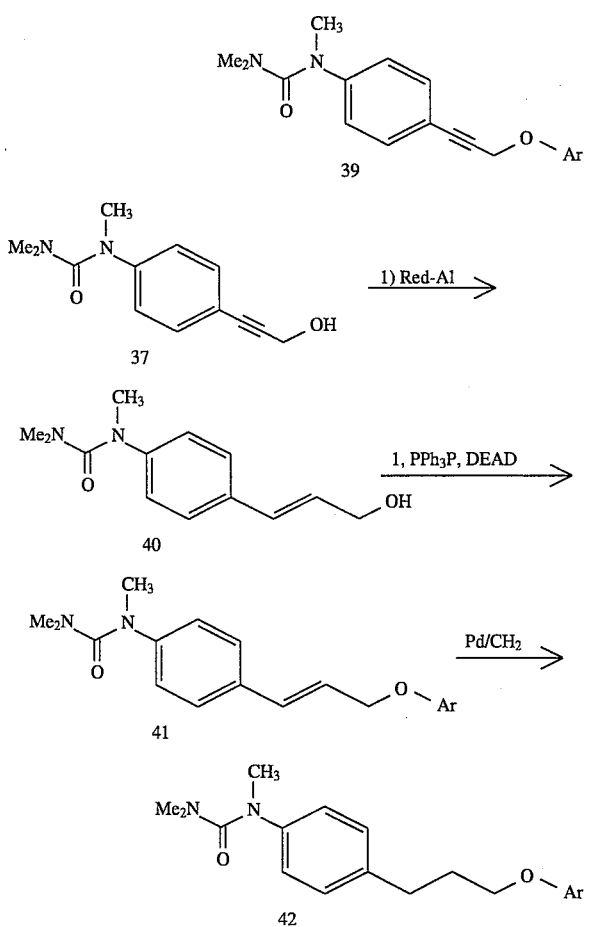

The foregoing may be better understood by the following examples, which are presented for illustration purposes only and are not intended to limit the scope of the invention.

EXAMPLE 1

Preparation of E- and Z-O-Methyl-4-[(3-(4-(N-acetyl-N-methylamino)benzyloxy)-5-fluoro-phenyl)oximinomethyl] tetrahydropyran.

Step 1. Preparation of 4-(N-acetyl-N-methylamino)benzoic acid.

To a solution of N-methyl-4-aminobenzoic acid (2.0 g, 13.2 mmol) dissolved in anhydrous pyridine (13.2 mL) was added acetic anhydride (1.4 mL, 14.5 mmol). The reaction was stirred at ambient temperature until TLC indicated complete reaction (~22 hours). The resulting solution was poured into ethyl acetate and the organic phase was washed (3×, 10% HCl; 1×, water; 1×, brine), dried (MgSO$_4$), filtered, and concentrated in vacuo to provide the corresponding amide as a colorless solid. Recrystallization (ethyl acetate/hexane) afforded pure 4-(N-acetyl-N-methylamino)benzoic acid (2.15 g, 84.0%). $^1$H NMR (300 MHz, CDCl$_3$) δ8.18 (2H, br d, J=8.5 Hz), 7.33 (2H, br d, J=8.5 Hz), 3.33 (3H, s), 2.0 (3H, br s). MS m/e 194 (M+H)$^+$, 211 (M+NH$_4$)$^+$.

Step 2. Preparation of 4-(N-acetyl-N-methylamino)benzyl alcohol.

An oven dried flask, under nitrogen flow, was charged with a stir bar, 4-(N-acetyl-N-methylamino)benzoic acid (1.0 g, 5.18 mmol), prepared as in step 1, anhydrous DME (10.3 mL), and anhydrous DMF (3.0 mL). The resulting solution was cooled to −20° C., and 4-methylmorpholine (0.60 mL, 5.4 mmol) and isobutyl chloroformate (0.70 mL, 5.4 mmol) were added sequentially via syringes. The reaction mixture was stirred under N$_2$ at −20° C. for 1 h. The resulting yellow mixture was filtered and the precipitate washed with DME (2×, ~1 mL). The combined filtrate and washings were cooled to 0° C. and a solution of sodium borohydride (800 mg, 21.1 mmol) in water (2.0 mL) was added dropwise. The reaction was stirred at 0° C. for 15 min. and quenched with saturated aqueous ammonium chloride. The resulting mixture was partitioned between ethyl acetate and brine. The combined organic layers were dried (MgSO$_4$), filtered and concentrated in vacuo to give an oil. Purification by flash chromatography on silica gel (90% ethyl acetate/hexane) provided the corresponding alcohol as a colorless oil which solidified on standing. Recrystallization from hexane provided 4-(N-acetyl-N-methylamino)benzyl alcohol as a colorless solid (543.0 mg, 58.5%). $^1$H NMR (300 MHz, CDCl$_3$) δ7.45 (2H, d, J=8.5 Hz), 7.18 (2H, d, J=8.5 Hz), 4.75 (2H, s), 3.27 (3H, s), 1.90 (3H, br s). MS m/e 180 (M+H)$^+$, 197 (M+NH$_4$)$^+$.

Step 3. Preparation of 4-(N-acetyl-N-methylamino)benzyl bromide.

To a solution of 4-(N-acetyl-N-methylamino)benzyl alcohol (543.0 mg, 3.0 mmol), prepared as in step 2, dissolved in dry CH$_2$Cl$_2$ (11.5 mL) was added dropwise 1M PBr$_3$ in CH$_2$Cl$_2$ (3.6 mL, 3.6 mmol) at 0° C. The reaction was stirred at ambient temperature until TLC indicated complete reaction (~5 hours). The resulting solution was partitioned between ethyl acetate and brine. The combined organic layers were decolorized with charcoal, dried (MgSO$_4$), filtered through celite and concentrated in vacuo. Purification by flash chromatography on silica gel (40% ethyl acetate/hexane) provided 4-(N-acetyl-N-methylamino)benzyl bromide as a colorless solid (595 mg, 81.0%). $^1$H NMR (300 MHz, CDCl$_3$) δ7.46 (2H, d, J=8.5 Hz), 7.18 (2H, d, J=8.5 Hz), 4.50 (2H, s), 3.27 (3H, s), 1.88 (3H, br s). MS m/e 242 (M+H)$^+$, 259/261 (M+NH$_4$)$^+$. Analysis calc'd for C$_{10}$H$_{12}$NOBr: C, 49.61; H, 5.00; N, 5.79. Found: C, 49.35; H, 4.97; N, 5.65.

Step 4. Tetrahydro-4H-pyran-4-(N,O-dimethyl)carboxamide.

A flask was charged with tetrahydro-4H-pyran-4-carboxylic acid (15.3 g, 118 mmol), prepared according to the method of J. v. Braun and Z. Kohler, *Chem. Ber.*, 50, 1657 (1917), dichloromethane (295 mL), and a stir bar. To the resulting solution was added 1 drop of dry dimethylformamide (DMF) and a solution of oxallyl chloride (15.5 mL, 178 mmol) in dichloromethane (47 mL). The reaction was stirred at ambient temperature for one hour and concentrated in vacuo. The resulting slurry was partially dissolved in dichloromethane (20 mL) and concentrated to dryness (2 cycles), then dried briefly under high vacuum. The acid chloride was suspended in dichloromethane (295 mL), cooled to 0° C. and a solution of N,O-dimethylhydroxylamine hydrochloride (12.7 g, 129 mmol) and pyridine (20.9 mL, 259 mmol) in dichloromethane (50 mL) was added. The reaction was quenched by adding excess 10% aqueous hydrochloric acid and stirring for three hours at ambient temperature. After separating the layers, the organic layer was washed with saturated aqueous NaHCO$_3$ and brine, dried over MgSO$_4$, filtered, and concentrated in vacuo to provide the corresponding amide as an orange liquid (18.9 g, 92%).

Step 5. 3-benzyloxy-5-fluorobromobenzene.

Sodium hydride (80% oil dispersion, 6.0 g, 201 mmol) was added slowly to a solution of benzyl alcohol (16 mL, 155 mmol) in THF (310 mL) at 0° C. DMF (300 mL) was added slowly and the reaction mixture was stirred until all of the NaH dissolved and gas evolution ceased. A solution of 1-bromo-3,5-difluorobenzene (30 g, 155 mmol) in THF (30 mL) was added and the reaction mixture was stirred for 30 min at ambient temperature. The reaction was quenched with saturated aqueous $NH_4Cl$, and the reaction mixture was extracted 3 times with ethyl acetate. The combined organic layers were washed with saturated aqueous $NH_4Cl$ and brine, dried over $MgSO_4$, filtered, and concentrated in vacuo to give a yellow liquid. 3- 3-benzyloxy-5-fluorobromobenzene (28 g) was isolated by chromatographyy on silica gel (5% ethyl acetate/hexanes).

Step 6. 4-[(3-benzyloxy-5-fluorophenyl)oxomethyl]tetrahydropyran.

An oven-dried flask was charged with 3-benzyloxy-5-flurobromobenzene, prepared as in step 5, freshly dried THF, and a stir bar. The flask was fitted with a septum, a nitrogen inlet, and a nitrogen outlet before cooling to −78° C. under a flow of nitrogen. To the cooled reaction mixture was added n-butyl lithium. The resulting solution was stirred at −78° C. for 0.5 hours after which a solution of tetrahydro-4H-pyran-4-(N,O-dimethyl)carboxamide (1.7 g, 10.62 mmol), prepared as in step 4, in THF was added. The reaction mixture was stirred 0.5 hours at −78° C., 0.5 hours at ambient temperature, and then quenched with water. The reaction mixture was partitioned between water and ethyl acetate. The organic layer was washed with saturated aqueous $NH_4Cl$ and brine, dried over $MgSO_4$, filtered and concentrated in vacuo. Pure 4-[(3-benzyloxy-5-fluorophenyl)oxomethyl] tetrahydropyran was obtained by chromatography on silica gel.

Step 7. 4-[(3-hydroxy-5-fluorophenyl)oxomethyl]tetrahydropyran.

To a suspension of palladium on carbon (1.5 g) in ethanol (30 mL) under $N_2$ was added a solution of 4-[(3-benzyloxy-5-flourophenyl)oxomethyl]-tetrahydropyran (3.7 g, 12 mmol), prepared as in step 6, in ethanol (70 mL). The reaction mixture was flushed three times with hydrogen, was then stirred for three hours under positive hydrogen pressure. The reaction mixture was flushed with $N_2$, filtered through a pad of celite, and concentrated in vacuo to yield 4-[(3-hydroxy-5-fluorophenyl)oxomethyl]tetrahydropyran (2.17 g, 81%) as a white powder which was used without further purification.

Step 8. 4-[(3-(4-N-acetyl-N-methylamino)benxyloxy)-5-fluoro-phenyl)oxomethyl]tetrahydropyran.

To a solution of 4-[(3-hydroxy-5-fluorophenyl)oxomethyl]tetrahydropyran (300 mg, 1.34 mmol), prepared as in step 7, in DMF (2.6 mL) was added NaH (60% oil dispersion, 107 mg, 2.68 mmol). The reaction mixture was stirred for one hour at ambient temperature, and then a solution of 4-(N-acetyl-N-methylamino) 4-(N-acetyl-N-methylamino)benzyl bromide (246 mg, 1.02 mmol) in DMF was added. The reaction mixture was stirred for 18 hours at ambient temperature and then was poured into an ethyl acetate, saturated aqueous $NH_4Cl$ mixture. The layers were separated, and the organic phase was washed once with saturated aqueous $NH_4Cl$, twice with brine, dried over $MgSO_4$, filtered, and concentrated in vacuo. Chromatography of silica gel (50% ethyl acetate/hexanes, then ethyl acetate) provided 4-[(3-(4-(N-acetyl-N-methylamino)benzyloxy-5-fluoro-phenyl)oxomethyl]tetrahydropyran as a yellow oil (248 mg, 63%).

Step 9. E- and Z-O-Methyl-4[(3-(4-(N-acetyl-N-methylamino)benzyloxy)-5-fluoro-phenyl)oximinomethyl]tetrahydropyran.

A solution of 4-[(3-(4-(N-acetyl-N-methylamino)benzyloxy)-5-fluorophenyl)oxomethyl]tetrahydropyran (220 mg, 0.60 mmol), prepared as in step 8, O-methylhydroxylamine hydrochloride (501 mg, 6.00 mmol), and sodium acetate (816 mg, 6.00 mmol) was stirred at 40°–50° C. for 24 hours. Additional O-methlhydroxylamine hydrochloride (6.00 mmol), and sodium acetate (6.00 mmol) were added and the reaction mixture was stirred for 72 hours at 50° C. and 4 hours at reflux. The reaction mixture was cooled to ambient temperature and was poured into an ethyl acetate, saturated aqueous $NH_4Cl$ mixture. The layers were separated, and the organic phase was washed once with saturated aqueous $NH_4Cl$, twice with brine, dried over $MgSO_4$, filtered, and concentrated in vacuo. Chromatography on silica gel (70% ethyl acetate/hexanes, then ethyl acetate) provided O-Methyl-4-[(3-4-(N-acetyl-N-methylamino)benzyloxy)-5-fluoro-phenyl)oximinomethyl]tetrahydropyran (92% mg, 39%) as a mixture of the E and Z oxime isomers. $^1$H NMR (300 MHz, $CDCl_3$) δ7.47 (2H, br d, J=8.5 Hz), 7.22 (2H, br d, J=8.5 Hz), 6.82–6.53 (3H, m, 5.08 and 5.05 (2H, 2s), 3.98 (2H, dt, J=12,3,3 Hz), 3.95 and 3.82 (3H, 2s), 3.34–3.52 (2.5H, m), 3.28 (3H, br s), 2.64 (0.5H, pentet, J=7.5 Hz), 1.90 (3H, br s), 1.54–1.72 (4H, m). MS m/e 415 (M+H)$^+$, 432 (M+$NH_4$)$^+$. Analysis calc'd for $C_{23}H_{27}FN_2O_4$: C, 66.65; H, 6.57; N, 6.76. Found: C, 66.94; H, 6.70; N, 6.49.

EXAMPLE 2

Preparation of E- and Z-4-[(3-(4-(N-acetyl-N-methylamino)benzyloxy)-5-fluoro-phenyl)oximinomethyl]tetrahydropyran.

The desired compound is prepared according to the method of Example 1, step 9, except substituting hydroxylamine hydrochloride for O-methylhydroxylamine hydrochloride.

EXAMPLE 3

Preparation of E- and Z-O-Methyl-4-[(3-(4-N-acetyl-N-methylamino)benzyloxy)phenyl)oximinomethyl]tetrahydropyran.

Step 1. 3-(methyloxymethoxy)bromobenzene.

To a solution of 3-bromophenol (27.4 g, 158 mmol) in $CH_2Cl_2$ was added chloromethyl methyl ether (18 mL, 237 mmol). The reaction mixture was cooled to 0° C. and diisopropylethylamine (55 mL, 316 mmol) was added and the cold bath was removed. The reaction mixture was stirred for 3 hours at ambient temperature and then poured into 10% aqueous HCl. The layers were separated and the aqueous phase was extracted 4 times with $CH_2Cl_2$. The combined organic layers were washed once each with saturated aqueous $NaHCO_3$, 15% aqueous NaOH, and brine, dried over $MGSO_4$, filtered, and concentrated in vacuo to provide 3-methyloxymethoxybromobenzene as a yellow oil.

Step 2. 4-[(3-methyloxymethoxyphenyl)oxomethyl]tetrahydropyran.

An oven-dried flask was charged with 3-methoxymethoxy)bromobenzene (2.29 g, 10.62 mmol), prepared as in step 1, freshly dried THF (43 mL), and a stir bar. The flask was fitted with a septum, a nitrogen inlet, and a nitrogen outlet before cooling to −78° C. under a flow of nitrogen. To the cooled reaction mixture was added n-butyl lithium (4.24 mL, 2.5M, 10.62 mmol in hexanes). The resulting solution was stirred at −78° C. for 0.5 hours after which a solution of tetrahydro-4H-pyran-4-(N,O-dimethyl)carboxamide (1.7 g, 10.62 mmol), prepared as in Example 1, step 4, in THF (10 mL) was added. The reaction mixture was stirred 0.5 hours at −78° C., 0.5 hours at ambient temperature, and then quenched with water. The reaction mixture was partitioned between water and ethyl acetate. The organic layer was washed with saturated ammonium chloride and brine, dried over MgSO$_4$, filtered and concentrated in vacuo to provide a yellow oil. Pure 4-[(3-methoxmethoxyphenyl)oxomethyl]tetrahydropyran (1.5 g, 57%) was obtained by chromatography on silica gel (30% ethyl acetate/hexanes).

Step 3. 4-[(3-hydroxyphenyl)oxomethyl]tetrahydropyran.

The methyloxymethoxy group was removed by treatment of 4-[(3-methyloxymethoxyphenyl)oxomethyl]tetrahydropyran (0.82 g, 3.27 mmol), prepared as in step 2 with concentrated hydrochloric acid (2.45 mL, 0.75 mL/mmol) in THF (13 mL) at ambient temperature for 0.5 hours. The reaction mixture was partitioned between water and ethyl acetate and the aqueous layer was extracted twice with ethyl acetate. The combined organic layers were washed with saturated aqueous sodium bicarbonate and brine, dried over MgSO$_4$, filtered, and concentrated in vacuo to provide 4-[(3-hydroxyphenyl)oxomethyl]tetrahydropyran as a brown solid (0.65 g, 96%) which was used without further purification.

Step 4. E- and Z-O-Methyl-4-[(3-(4-(N-acetyl-N-methylamino)benzyloxy)phenyl)oximinomethyl]tetrahydropyran.

The desired compound is prepared according to the method of Example 1, steps 8 and 9, except substituting 4-[(3-hydroxyphenyl)oxomethyl]tetrahydropyran for 4-[(3-hydroxy-5-fluorophenyl)oxomethyl]tetrahydropyran

EXAMPLE 4

Preparation of E- and Z-4-[(3-(4-(N-acetyl-N-methylamino)benzyloxy)phenyl)oximinomethyl]tetrahydropyran.

The desired compound is prepared according to the method of Example 2, except substituting 4-[(3-(4-(N-acetyl-N-methylamino) benzyloxy)phenyl)oxomethyl]tetrahydropyran, prepared as in Example 3, for 4-[(3-(4-(N-acetyl-N-methylamino)benzyloxy)-5-fluorophenyl)oxomethyl]tetrahydropyran.

EXAMPLE 5

Preparation of E- and Z-O-Methyl-4-[(3-(4-N',N'-dimethylaminocarbonyl-N-methylamino)benzyloxy)-5-fluoro-phenyl)oximinomethyl]tetrahydropyran. Step 1. Preparation of methyl 4-(N-methylaminocarbonyl)aminobenzoate.

A solution of methyl 4-aminobenzoate (15 g, 99 mmol), and methyl isocyanate (11.8 mL, 200 mmol) in toluene (400 mL) was heated at 100° C. under N$_2$ for 3 hours during which time a precipitate formed slowly. Additional methyl isocyanate (11.8 mL, 200 mmol) was added and heating was continued for 2 hours. The reaction mixture was cooled to 0° C. and filtered. The precipitate was washed with ether and vacuum-dried to give methyl 4-(N-methylaminocarbonyl)aminobenzoate as a colorless solid (17.5 g, 85%).

Step 2. Preparation of methyl 4(N',N'-dimethylaminocarbonyl-N-methylamino)benzoate.

To a 0° C. suspension of NaH (80% oil dispersion, 3.60 g, 120 mmol) in THF (200 mL) under N$_2$ was added a solution of methyl 4-(N-methylaminocarbonyl)aminobenzoate (10.0 g, 48 mmol), prepared as in step 1, in THF (40 mL). The reaction mixture was stirred at 0° C. until gas evolution ceased, then the cold bath was removed and stirring was continued for 1.5 hours. A solution of iodomethane (6.6 mL, 106 mmol) in DMF (24 mL) was added and the reaction mixture was stirred for 72 hours at ambient temperature. NaH (2.0 g), and iodomethane (5.0 mL) were then added and the reaction mixture was stirred for an additional 2 hours. The reaction mixture was poured slowly into ice-water and the organics were stripped off in vacuo. The aqueous solution was extracted with ethyl acetate (10x). The combined organic layers were dried over MgSO$_4$, filtered, and concentrated. Pure methyl 4-(N',N'-dimethylaminocarbonyl-N-methylamino)benzoate (6.62 g, 58%) was obtained as a colorless oil which crystallized on standing after chromatography on silica gel (40%, then 50% ethyl acetate/hexanes). mp 71°–73° C.

Step 3. Preparation of 4N',N'-dimethylaminocarbonyl-N-methylamino)benzyl alcohol.

To a 0° C. solution of methyl 4(N', 4(N',N'-dimethylaminocarbonyl-N-methylamino)benzoate (1.50 g, 6.35 mmol), prepared as in step 2 in THF (11.4 mL) was added lithium triethylborohydride (1.0M solution in THF, 14 mmol). The reaction mixture was stirred for 1 hour. Water (3.0 mL) and H$_2$O$_2$ (30% aqueous solution, 5.0 mL) were added cautiously and the reaction mixture was stirred at 45° C. for 20 min. Aqueous HCL (6M, 8.0 mL) was added and the reaction mixture was stirred at reflux for 14 hours. The reaction mixture was cooled to ambient temperature and poured into ethyl acetate. The aqueous phase was extracted three times with ethyl acetate. The combined organic layers were dried over MgSO$_4$, filtered, and concentrated in vacuo. 4-(N',N'-dimethylaminocarbonyl-N-methylamino)benzyl alcohol (797 mg, 61%) was isolated as a colorless solid by chromatography on silica gel (ethyl acetate). mp 65°–66° C.

Step 4. Preparation of 4-(N',N'-dimethylaminocarbonyl-N-methylamino)benzyl chloride.

To a stirred solution at −23° C. under N$_2$ of 4-(N',N'-dimethylaminocarbonyl-N-methylamino)benzyl alcohol (77.0 mg, 0.37 mmol), prepared as in step 4, in dry CH$_2$Cl$_2$ (3.7 mL) was added triethylamine (67.0 µL, 0.48 mmol), and methanesulfonyl chloride (34.0 µL, 0.44 mmol). The reaction mixture was stirred at ambient temperature until TLC indicated complete reaction (~5 hours). The resultant solution was poured into ethyl acetate and the organic phase was washed (2 X, water; 2×, brine), dried (MgSO$_4$), filtered and concentrated in vacuo. Purification by flash chromatography on silica gel (70% ethyl acetate/hexane) provided 4-(N',N'-dimethylaminocarbonyl-N-methylamino)benzyl chloride (56.0 mg, 67.0%) as a colorless oil which crystallized on standing at −25° C. mp 38.5°–39° C. $^1$H NMR (300 MHz, CDCl$_3$) δ7.34 (2H, d, J=8.5 Hz), 7.04 (2H, d, J=8.5 Hz), 4.57 (2H, s), 3.22 (3H, s), 2.71 (6H, s). MS m/e 227 (M+H$^+$, 244 (M+NH$_4$)$^+$.

Step 5, E- and Z-O-Methyl-4-[(3-(4-(N',N'-dimethylaminocarbonyl-N-methylamino)benzyloxy)-5-fluorophenyl)oximinomethyl]tetrahydropyran.

The desired compound is prepared as a 1:1 mixture of E:Z isomers according to the method of Example 1, steps 8 and 9, except substituting 4-(N',N'-dimethylaminocarbonyl-N-methylamino)benzyl chloride, prepared as in step 4, for 4-(N-acetyl-N-methylamino)benzyl bromide. $^1$H NMR (300 MHz, CDCl$_3$) δ7.38 (2H, d, J=8 Hz), 7.07 (2H, d, J=8 Hz), 6.53–6.80 (3H, m), 5.01 and 4.98 (2H, 2s), 3.98 (2H, br m), 3.93 and 3.82 (3H, 2s), 2.72 (6H, s), 2.60–2.72 (0.5H, m), 1.89 (1H, dq, J=4.5, 13.5, 13.5, 13.5 Hz), 1.54–1.71 (3H, m). MS m/e 444 (M+H)$^+$, 461 (M+NH$_4$)$^+$. Analysis calc'd for C$_{24}$H$_{30}$FN$_3$O$_4$: C, 64.99; H, 6.82; N, 9.47. Found: C, 65.08; H, 6.70; N, 9.31.

EXAMPLE 6

Preparation of E- and Z-4-[(3-(4-(N',N'-dimethylaminocarbonyl-N-methylamino)-benzyloxy)-5-fluoro-phenyl)oximinomethyl]tetrahydropyran.

The desired compound is prepared according to the method of Example 2, except substituting 4[(3-(4-(N',N'-dimethylaminocarbonyl-N-methylamino)benzyloxy)-5-fluoro-phenyl)oximinomethyl]tetrahydropyran, prepared as in Example 5, for 4-[(3-(4-(N-acetyl-N-methylamino)benzyloxy)-5-fluoro-phenyl)oxomethyl]tetrahydropyran.

EXAMPLE 7

Preparation of E- and Z-O-Methyl-4[(3-(4-(N',N'-dimethylaminocarbonyl-N-methylamino)benzyloxy)phenyl)oximinomethyl]tetrahydropyran.

The desired compound is prepared according to the method of Example 5, except substituting 4-[(3-hydroxyphen-1-yl)oxomethyl]tetrahydropyran, prepared as in Example 3, for 4-[(3-hydroxy-5-fluorophen-1-yl)oxomethyl]tetrahydropyran.

EXAMPLE 8

Preparation of E- and Z-4-[(3-(4-(N',N'-dimethylaminocarbonyl-N-methylamino)-benzyloxy)phen-1-yl)oximinomethyl]tetrahydropyran.

The desired compound is prepared according to the method of Example 2, except substituting 4-[(3-(4-(N',N'-dimethylaminocarbonyl-N-methylamino)benzyloxy)phenyl)oxomethyl]tetrahydropyran, prepared as in Example 7, for 4-[(3-(4-(N-acetyl-N-methylamino)benzyloxy)-5-fluoro-phenyl)oxomethyl]tetrahydropyran.

EXAMPLE 9

Preparation of E- and Z-O-Methyl-4-[(3-(4-(N',N'-dimethylaminocarbonyl-N-methylamino)benzylamino)phenyl)oximinomethyl]tetrahydropyran.

Step 1. Preparation of N-t-Boc-3-bromoaniline.

3-bromoaniline (10 g, 58.1 mmol) and di-tert-butyldicarbonate (19.0 g, 87.1 mmol) were dissolved in 2M aqueous sodium hydroxide and heated at reflux for 1 hour. After cooling to ambient temperature, the reaction mixture was extracted with ethyl acetate. The organic layer was washed (saturated aqueous ammonium chloride, 1x; water, 1x; and brine, 2x), dried (MgSO$_4$), filtered, concentrated in vacuo, and dried under high vacuum to provide N-t-Boc-3 bromoaniline as a colorless solid (15.8 g, 100%). mp 83° C. $^1$H NMR (300 MHz, CDCl$_3$) δ7.66 (1H,br m), 7.08–7.23 (3H, m), 6.46 (1H, br s), 1.52 (9H, s). MS m/e 272/274 (M+H)$^+$, 289/291 (M+NH$_4$)$^+$.

Step 2. Preparation of 4-[(3-t-butyloxycarbonylaminophenyl)oxomethyl]-tetrahydropyran.

The desired compound is prepared according to the method of Example 1, step 6, except substituting N-t-Boc-3 bromoaniline. prepared as in step 1, for 3-benzyloxy-5-fluorobromobenzene.

Step 3. Preparation of 4-[(3-aminophenyl)oxomethyl]tetrahydropyran.

The desired compound is prepared by reaction of a solution in CH$_2$Cl$_2$ of 4-[(3-t-butyloxycarbonylaminophenyl)oxomethyl]tetrahydropyran, prepared as in step 2, with trifluoroacetic acid.

Step 4. Preparation of E and Z-O-Methyl-4-[(3-(4-(N',N'-dimethylaminocarbonyl-N-methylamino)benzylamino)phenyl)oxomethyl]tetrahydropyran.

The desired compound is prepared according to the method of Example 5, step 5, except substituting 4-(3-aminophenyl)-4-methoxytetrahydropyran, prepared as in step 3, for 4-[(3-hydroxy-5-fluorophenyl)oxomethyl]tetrahydropyran.

EXAMPLE 10

Preparation of E- and Z-O-Methyl-4-[(3-(4-N-acetyl-N-methylamino)benzylamino)phenyl)oximinomethyl]tetrahydropyran.

The desired compound is prepared according to the method of Example 9, except substituting 4-(N-acetyl-N-methylamino)benzyl bromide, prepared as in Example 1, step 3, for 4-(N',N'-dimethylaminocarbonyl-N-methylamino)benzyl chloride.

EXAMPLE 11

Preparation of E and Z-O-Methyl-4-[(3-(4-(N-acetyl-N-methylamino)phenylthio)phenyl)-oximinomethyl]tetrahydropyran.

Step 1. Preparation of N-t-Boc-4-bromoaniline.

The desired compound is prepared according to the method of Example 9, step 1, except substituting 4-iodoaniline for 3-bromoaniline.

Step 2. Preparation of 3-(4-(t-butyloxycarbonylamino)phenylthio)bromobenzene.

The desired material is prepared by reaction of N-t-Boc-4-iodoaniline, prepared as in step 1, and 3-bromothiophenol in the presence of copper(I) iodide.

Step 3. Preparation of 3-(4-aminophenylthio)bromobenzene.

The desired material is prepared according to the method of Example 9, step 3, except substituting 3-(4-(t-butyloxycarbonylamino)phenylthio)bromobenzene, prepared as in step 2, for 4-[(3-t-butyloxycarbonylaminophenyl)oxomethyl]tetrahydropyran.

Step 4. Preparation of 3-(4-(N-acetylamino)phenylthio)bromobenzene.

The desired compound is prepared according to the method of Example 1, step 1, except substituting 3-(4-aminophenylthio)bromobenzene prepared as in step 3, for N-methyl-4-aminobenzoic acid.

Step 5. Preparation of 3-(4-(N-acetyl-N-methylamino)phenylthio)bromobenzene.

The desired compound is prepared according to the method of Example 5, step 3, except substituting 3-(4-(N-acetylamino)phenylthio)bromobenzene, prepared as in step 4, for 4-(N-methylaminocarbonyl)aminobenzoate.

Step 6. Preparation of 4[(3-(4-(N-acetyl-N-methylamino)phenylthio)phenyl)oxomethyl]-tetrahydropyran.

The desired compound is prepared according to the method of Example 1, step 6 except substituting 3-(4-(N-acetyl-N-methylamino)phenylthio)bromobenzene, prepared as in step 5, for 3-benzyloxy-5-fluorobromobenzene.

Step 7. Preparation of E and Z-O-Methyl-4-[(3-(4-(N-acetyl-N-methylamino)phenylthio)phenyl)oximinomethyl] tetrahydropyran.

The desired compound is prepared according to the method of Example 1, step 9, except substituting 4-[(3-(4-(N-acetyl-N-methylamino)phenylthio)phenyl)oxomethyl]-tetrahydropyran, prepared as in step 6, for 4-[(3-(4-(N-acetyl-N-methylamino)benzyloxy)-5-fluorophen-1-yl)oxomethyl]tetrahydropyran.

EXAMPLE 12

Preparation of Preparation of E and Z-4-[(3-(4-(N-acetyl-N-methylamino)phenylthio)-phenyl)oximinomethyl]tetrahydropyran.

The desired compound is prepared according to the method of Example 2, except substituting 4-[(3-(4-(N-acetyl-N-methylamino)phenylthio)phenyl)oxomethyl]tetrahydropyran, prepared as in Example 11, step 6, for 4-[(3-(4-(N-acetyl-N-methylamino)benzyloxy)-5-fluorophen-1-yl)oxomethyl]tetrahydropyran.

EXAMPLE 13

Preparation of E- and Z-O-Methyl-4-8 (3-(4-(N',N'-dimethylaminocarbonyl-N-methylamino)benzylthio)phenyl)oximinomethyl]tetrahydropyran. Step 1. Preparation of 4-[(3-thiophenyl)oxomethyl]tetrahydropyran.

The desired material is prepared according to the method of Example 3, step 2, except substituting 3-bromothiophenol for 3-(methoxymethoxy)bromobenzene, and using 2.2 equiv. of n-BuLi.

Step 2. Preparation of E- and Z-O-Methyl-4-[(3-(4-(N',N'-dimethylaminocarbonyl-N-methylamino)benzylthio)phenyl)oximinomethyl]tetrahydropyran.

The desired compound is prepared according to the method of Example 5, except substituting 4-[(3-thiophenyl)oxomethyl]tetrahydropyran, prepared as in step 1, for 4-[(3-hydroxy-5-fluorophenyl)oxomethyl]tetrahydropyran.

EXAMPLE 14

Preparation of E- and Z-4-[(3-(4-(N',N'-dimethylaminocarbonyl-N-methylamino)benzylthio)phenyl)oximinomethyl]tetrahydropyran.

The desired compound is prepared according to the method of Example 2, except substituting 4-[(3-(4-(N',N'-dimethylaminocarbonyl-N-methylamino)-benzylthio)phenyl)oxomethyl]tetrahydropyran, prepared as in Example 13, for 4-[(3-(4-(N-acetyl-N-methylamino)benzyloxy)-5-fluorophen-1-yl)oxomethyl]tetrahydropyran.

EXAMPLE 15

Preparation of E- and Z-O-Methyl-4-[(3-(4-(N-acetyl-N-methylamino)benzylthio)-phenyl)oximinomethyl]tetrahydropyran.

The desired compound is prepared according to the method of Example 1, steps 8 and 9, except substituting 4-[(3-thiophenyl)oxomethyl]tetrahydropyran, prepared as in Example 13, step 1, for 4-[(3-hydroxy-5-fluorophenyl)oxomethyl]tetrahydropyran.

EXAMPLE 16

Preparation of E- and Z-4-[(3-(4-(N-acetyl-N-methylamino)benzylthio)phenyl)oximinomethyl]tetrahydropyran.

The desired compound is prepared according to the method of Example 2, except substituting 4-[(3-(4-(N-acetyl-N-methylamino)-benzylthio)phenyl)oxomethyl]tetrahydropyran, prepared as in Example 15, for 4-[(3-(4-(N-acetyl-N-methylamino)benzyloxy)-5-fluorophen-1-yl)oxomethyl]tetrahydropyran.

EXAMPLE 17

Preparation of E- and Z-O-Methyl-4-[(3-(4-(N-acetyl-N-methylamino)benzylthio)-5-fluorophenyl)oximinomethyl]tetrahydropyran.

The desired compound is prepared according to the method of Example 1, except substituting α-toluenethiol for benzyl alcohol.

EXAMPLE 18

Preparation of E- and Z-4-[(3-(4-(N-acetyl-N-mehtylamino)benzylthio)-5-fluorophenyl)oximinomethyl]tetrahydropyran.

The desired compound is prepared according to the method of Example 2, except substituting 4-[(3-(4-(N-acetyl-N-mehtylamino)benzylthio-5-fluorophenyl)oxomethyl]tetrahydropyran, prepared as in Example 17, for 4-[(3-(4-(N-acetyl-N-methylamino)benzyloxy)-5-fluorophen-1-yl)oxomethyl]tetrahydropyran.

EXAMPLE 19

Preparation of E- and Z-O-Methyl-4[(3-(4-N-thioacetyl-N-methylamino)benzylthio)-5-fluorophenyl)oximinomethyl] tetrahydropyran.

The desired compound is prepared by treatment of E- and Z-O-methyl -4-[(3-(4-(N-acetyl-N-methylamino)benzylthio)-5-fluorophenyl)oxomethyl]tetrahydropyran, prepared as in Example 17, with Lawesson's Reagent ([2,4-bis (4-methoxyphenyl)-1,3-dithia-2,4-diphosphetane-2,4-disulfide) according to the method of Katah, A., Kashima, C., and Omote, Y. *Heterocycles*, 1982, 19(12), 2283.

EXAMPLE 20

Preparation of E- and Z-O-Methyl-4-[(3-(4-(N',N'-dimethylaminothiocarbonyl-N-methylamino)benzylthio)phenyl)oximinomethyl]tetrahydropyran.

The desired compound is prepared according to the method of Example 19, except substituting E- and Z-O-methyl-4-[(3-(4-(N',N'-dimethylaminothiocarbonyl-N-methylamino)benzyloxy)-5-fluorophen-1-yl)oxomethyl]tetrahydropyran, prepared as in Example 13, for E- and Z-O-Methyl-4-[(3-(4-(N-acetyl-N-methylamino)benzylthio)-5-fluorophenyl)oxomethyl]tetrahydropyran.

EXAMPLE 21

Preparation of E and Z-O-Methyl-4-[(3(4-N-acetyl-N-methylamino)phenylsulfinyl)phenyl)oximinomethyl]tetrahydropyran.

The desired compound is prepared by treatment of E and Z-O-Methyl-4-[(3-(4-(N-acetyl-N-methylamino)phenylthio)phenyl)oximinomethyl]tetrahydropyran, prepared as in Example 11, with sodium metaperiodate as described in EPA 409 413.

EXAMPLE 22

Preparation of E and Z-O-Methyl-4-[(3-(4-(N-acetyl-N-methylamino)phenylsulfonyl)phenyl)oximinomethyl]tetrahydropyran.

The desired compound is prepared by treatment of E and Z-O-Methyl-4-[(3-(4-(N-acetyl-N-methylamino)phenylthio)phenyl)oximinomethyl]tetrahydropyran, prepared as in Example 11, with potassium peroxymonosulphate as described in EPA 409 413.

EXAMPLE 23

Preparation of E- and Z-O-Methyl-4-[(3-(4-((N',N'-dimethylaminocarbonyl)aminomethyl)benzyloxy)-5-fluorophenyl)oximinomethyl]tetrahydropyran.

Step 1. Preparation of 4-[(3-(4-bromomethylbenzyloxy)-5-fluorophenyl)oxomethyl]tetrahydropyran.

The desired compound is prepared according to the method of Example 1, step 8, except substituting α,α'-dibromo-p-xylene for 4-(N-acetyl-N-methylamino)benzyl bromide.

Step 2. Preparation of 4-[(3-(4-N',N'-dimethylaminocarbonyl)aminomethyl)benzoyloxy)-5-fluorophenyl)oxomethyl]tetrahydropyran.

The desired material is prepared by reaction of a solution of 1,1-dimethylurea in DMF with NaH and 4-[(3-(4-bromomethylbenzyloxy)-5-fluorophenyl)oxomethyl]tetrahydropyran which is prepared as described in step 1.

Step 3. Preparation of E- and Z-O-Methyl-4-[(3-(4-((N',N'-dimethylaminocarbonyl)aminomethyl)benzyloxy)-5-fluorophenyl)oximinomethyl]-tetrahydropyran.

The desired compound is prepared according to the method of Example 1, step 9, except substituting 4-[(3-(4-((N',N'-dimethylaminocarbonyl)aminomethyl)benzyloxy)phenyl)oxomethyl]tetrahydropyran, prepared as in step 2, for 4-[(3-(4-(N-acetyl-N-methylamino)benzyloxy)-5-fluorophenyl)oxomethyl]tetrahydropyran.

EXAMPLE 24

Preparation of E and Z-O-Methyl-4-[(3-(4-(N-acetyl)aminomethyl)benzyloxy)-5-fluorophenyl)oximinomethyl]tetrahydropyran.

The desired compound is prepared according to the method of Example 23, except substituting acetamide for 1,1-dimethylurea.

EXAMPLE 25

Preparation of E- and Z-O-Methyl-4-[(3-(4-(((N',N'-dimethylaminocarbonyl-N-methylamino)methyl)benzyloxy)-5-fluorophenyl)oximinomethyl]tetrahydropyran.

Step 1. Preparation of 4-[(3-(4-((N',N'-dimethylaminocarbonyl-N-methylamino)methyl)benzyloxy)-5-fluorophenyl)oxomethyl]tetrahydropyran.

The desired compound is prepared according to the method of Example 5, step 2, except substituting 4-[(3-(4-((N',N'-dimethylaminocarbonyl)aminomethyl)benzyloxy)-5-fluorophenyl)oxomethyl]tetrahydropyran, prepared as in Example 23, for methyl 4-(N-methylaminocarbonyl)aminobenzoate.

Step 2. Preparation of E- and Z-O-methyl-4[(3-(4-(((N',N'-dimethylaminocarbonyl)-N-methylamino)methyl)benzyloxy)-5-fluorophenyl)oximinomethyl]tetrahydropyran.

The desired compound is prepared according to the method of Example 1, step 9, except substituting 4-[(3-(4-(((N',N'-dimethylaminocarbonyl)-N-methylamino)methyl)benzyloxy)phenyl)oxomethyl]tetrahydropyran, prepared as in step 2, for 4-[(3-(4-(N-acetyl-N-methylamino)benzyloxy)-5-fluorophenyl)oxomethyl]tetrahydropyran.

EXAMPLE 26

Preparation of E and Z-O-Methyl-4-[(3-(4-(N-acetyl-N-methyl)aminomethyl)benzyloxy)-5-fluorophenyl)oximinomethyl]tetrahydropyran.

The desired compound is prepared according to the method of Example 25, except substituting 4-[(3-(4-(N-acetyl)aminomethyl)benzyloxy)-5-fluorophenyl)oxomethyl]tetrahydropyran, prepared as in Example 24, for 4-[(3-(4-((N',N'-dimethylaminocarbonyl)aminomethyl)benzyloxy)-5-fluorophenyl)oxomethyl]tetrahydropyran.

EXAMPLE 27

Preparation of E- and Z-O-Methyl-4-[(3-(4-((N',N'-dimethylaminocarbonyl)aminomethyl)benzyloxy)phenyl)oximinomethyl]tetrahydropyran.

The desired compound is prepared according to the method of Example 23, except substituting 4-[(3-hydroxyphenyl)oxomethyl]tetrahydropyran, prepared as in Example 3, step 3, for 4-[(3-hydroxy-5-fluorophenyl)oxomethyl]tetrahydropyran.

EXAMPLE 28

Preparation of E and Z-O-Methyl-4-[(3-(4-(N-acetyl)aminomethyl)benzyloxy)phenyl)oximinomethyl]tetrahydropyran.

The desired compound is prepared according to the method of Example 24, except substituting 4-[(3-hydroxyphenyl)oxomethyl]tetrahydropyran, prepared as in Example 3, step 3, for 4-[(3-hydroxy-5-fluorophenyl)oxomethyl]tetrahydropyran.

EXAMPLE 29

Preparation of E- and Z-O-Methyl-4-[(3-(4-(((N',N'-dimethylaminocarbonyl)-N-methylamino)methyl)benzyloxy)phenyl)oximinomethyl]tetrahydropyran.

The desired compound is prepared according to the method of Example 25, except substituting 4-[(3-hydroxyphenyl)oxomethyl]tetrahydropyran, prepared as in Example 3, step 3, for 4-[(3-hydroxy-5-fluorophenyl)oxomethyl]tetrahydropyran.

EXAMPLE 30

Preparation of E and Z-O-Methyl-4-[(3-(4-(N-acetyl-N-methyl)aminomethyl)benzyloxy)phenyl)oximinomethyl]tetrahydropyran.

The desired compound is prepared according to the method of Example 26, except substituting 4-[(3-hydroxyphenyl)oxomethyl]tetrahydropyran, prepared as in Example 3, step 3, for 4-[(3-hydroxy-5-fluorophenyl)oxomethyl]tetrahydropyran.

EXAMPLE 31

Preparation of E- and Z-O-Methyl-4-[(3-((N',N'-dimethylaminocarbonyl)aminomethyl)benzylthio)-5-fluorophenyl)oximinomethyl]-tetrahydropyran.

The desired compound is prepared according to the method of Example 23, except substituting 4-[93-thioxy-5-fluorophenyl)oxomethyl]tetrahydropyran, prepared as in Example 17, for 4-[(3-hydroxy-5-fluorophenyl)oxomethyl]tetrahydropyran.

EXAMPLE 32

Preparation of E- and Z-O-Methyl-4-[(3-(4-((N',N'-dimethylaminocarbonyl)aminomethyl)benzylthio)phenyl)oximinomethyl]tetrahydropyran.

The desired compound is prepared according to the method of Example 23, except substituting 4-[(3-thiophenyl)oxomethyl]tetrahydropyran, prepared as in Example 13, step 1, for 4-[(3-hydroxy-5-fluorophenyl)oxomethyl]tetrahydropyran.

EXAMPLE 33

Preparation of E- and Z-O-Methyl-4-[(3-(4-(((N',N'-dimethylaminocarbonyl)-N-methylamino)methyl)benzylthio)-5-fluorophenyl)oximinomethyl]tetrahydropyran.

The desired compound is prepared according to the method of Example 25, except substituting 4-[(3-(4-((N',N'-dimethylaminocarbonyl)aminomethyl)benzylthio)-5-fluorophenyl)oxomethyl]-tetrahydropyran, prepared as in Example 31, for 4-[(3-(4-((N',N'-dimethylaminocarbonyl)aminomethyl)benzyloxy)-5-fluorophenyl)oxomethyl]tetrahydropyran.

EXAMPLE 34

Preparation of E- and Z-O-Methyl-4-[(3-(4-(((N',N'-dimethylaminocarbonyl)-N-methylamino)methyl)benzylthio)phenyl)oximinomethyl]tetrahydropyran.

The desired compound is prepared according to the method of Example 25, except substituting 4-[(3-(4-((N',N'-dimethylaminocarbonyl)aminomethyl)benzylthio)phenyl)oxomethyl]tetrahydropyran, prepared as in Example 32, for 4-[(3-(4-((N',N'-dimethylaminocarbonyl)aminomethyl)benzyloxy)-5-fluorophenyl)oxomethyl]tetrahydropyran.

EXAMPLE 35

Preparation of E and Z-O-Methyl-4-[(3-(4-(N-acetyl)aminomethyl)benzylthio)-5-fluorophenyl)oximinomethyl]tetrahydropyran.

The desired compound is prepared according to the method of Example 24, except substituting 4-[(3-thioxy-5-fluorophenyl)oxomethyl]tetrahydropyran, prepared as in Example 17, for 4-[(3-hydroxy-5-fluorophenyl)oxomethyl] tetrahydropyran.

EXAMPLE 36

Preparation of E and Z-O-Methyl-4-[(3-(4-(N-acetyl)aminomethyl)benzylthio)phenyl)oximinomethyl]tetrahydropyran.

The desired compound is prepared according to the method of Example 24, except substituting 4-[(3-thiophenyl)oxomethyl[tetrahydropyran, prepared as in Example 13, step 1, for 4-[(3-hydroxy-5-fluorophenyl)oxomethyl]tetrahydropyran.

EXAMPLE 37

Preparation of E and Z-O-Methyl-4-[(3-(4-(N-acetyl-N-methyl)aminomethyl)benzylthio)-5-fluorophenyl)oximinomethyl]tetrahydropyran.

The desired compound is prepared according to the method of Example 26, except substituting 4-[(3-(4-(N-acetyl)aminomethyl)benzylthio)-5-fluorophenyl)oximinomethyl]tetrahydropyran, prepared as in Example 35, for 4-[(3-(4-(N-acetyl)aminomethyl)benzyloxy)-5-fluorophenyl)oxomethyl]tetrahydropyran.

EXAMPLE 38

Preparation of E and Z-O-Methyl-4-[(3-(4-(N-acetyl-N-methyl)aminomethyl)benzylthio)phenyl)oximinomethyl]tetrahydropyran.

The desired compound is prepared according to the method of Example 26, except substituting 4-[(3-(4-(N-acetyl)aminomethyl)benzylthio)phenyl)oximinomethyl]tetrahydropyran, prepared as in Example 36, for 4-[(3-(4-(N-acetyl)aminomethyl)benzyloxy)-5-fluorophenyl)oxomethyl]tetrahydropyran.

EXAMPLE 39

Preparation of E and Z-O-Methyl-4-[(3-(4-(imidazolidin-2-on-1-ylmethyl)benzyloxy)-5-fluorophenyl)oximinomethyl] tetrahydropyran.

The desired compound is prepared according to the method of Example 23, except substituting 2-imidazolidinone for 1,1-dimethylurea.

EXAMPLE 40

Preparation of E and Z-O-Methyl-4-[(3-(4-(imidazolidin-2-on-1-ylmethyl)benzyloxy)phenyl)oximinomethyl]tetrahydropyran.

The desired compound is prepared according to the method of Example 39, except substituting 4-[(3-hydroxyphenyl)oxomethyl]tetrahydropyran, prepared as in Example 3, step 3, for 4-[(3-hydroxy-5-fluorophenyl)oxomethyl]tetrahydropyran.

EXAMPLE 41

Preparation of E and Z-O-Methyl-4-[(3-(4-(imidazolidin-2-on-1-ylmethyl)benzylthio-5-fluorophenyl)oximinomethyl] tetrahydropyran.

The desired compound is prepared according to the method of Example 39, except substituting 4-[(3-thioxy-5-fluorophenyl)oxomethyl]tetrahydropyran, prepared as in Example 17, for 4-[(3-hydroxy-5-fluorophenyl)oxomethyl] tetrahydropyran.

EXAMPLE 42

Preparation of E and Z-O-Methyl-4-[(3-(4-imidazolidin-2-on-1-ylmethyl)benzylthio)phenyl)oximinomethyl]tetrahydropyran.

The desired compound is prepared according to the method of Example 39, except substituting 4-[(3-thioxyphenyl)oxomethyl]tetrahydropyran, prepared as in Example 13, step 1, for 4-[(3-hydroxy-5-fluorophenyl)oxomethyl]tetrahydropyran.

EXAMPLE 43

Preparation of E- and Z-O-Methyl-4-[(3-(3-(N',N'-dimethylaminocarbonyl-N-methylamino)-benzyloxy)-5-fluoro-phenyl)oximinomethyl]tetrahydropyran.

Step 1. Preparation of 3-(O-t-butyldimethylsilyloxymethyl)aniline.

To a solution of 3-aminobenzyl alcohol (2.00 g, 16.2 mmol) and tert-butyldimethylsilyl chloride (2.90 g, 19.4 mmol) in $CH_2Cl_2$ (32.5 mL) was added triethylamine (7.45 mL, 53.5 mmol). The reaction mixture was stirred for 18 hours at ambient temperature and was then partitioned between ethyl acetate and $H_2O$. The organic phase was washed twice with $H_2O$, twice with brine, dried over $MgSO_4$, filtered, and concentrated in vacuo. 3-(O-t-butyldimethylsilyloxymethyl)aniline (2.18 g, 57%) was obtained as a yellow oil by chromatography on silica gel (30% ethyl acetate/hexane). $^1H$ NMR (300 MHz, $CDCl_3$) δ7.10 (1H, t, J=7.5 Hz), 6.67–6.72 (2H, m), 6.56 (1H, br d, J=7.5 Hz), 4.66 (2H, s), 3.63 (2H, br s), 0.94 (9H, s), 0.09 (6H, s). MS m/e 238$(M+H)^+$, 255 $(M+NH_4)^{30}$.

Step 2. Preparation of O-t-butyldimethylsilyl-3-[(N'-methylaminocarbonyl)amino]benzyl alcohol.

To a solution under $N_2$ of 3-(O-t-butyldimethylsilyloxymethyl)aniline (900 mg, 3.79 mmol) in toluene (7.6 mL) was added methylisocyanate (0.45 mL, 7.58 mmol). The reaction mixture was stirred at 100° C. for 1.5 hours and was then cooled to ambient temperature and partitioned between ethyl acetate and $H_2O$. The organic phase was washed once with $H_2O$, twice with brine, dried over $MgSO_4$, filtered, and concentrated in vacuo. The oily residue crystallized on standing. The crystalline solid was washed twice with hexane to provide O-t-butyldimethylsilyl-3-[(N'-methylaminocarbonyl)amino]benzyl alcohol (641 mg, 57%). mp 110°–113° C. $^1$H NMR (300 MHz, CDCl$_3$) δ7.23–7.28 (2H, m), 7.17 (1H, d, J=7.5 Hz), 7.03 (1H, d, J=7.5 Hz), 6.68 (1H, br s), 5.0 (1H, br q, J=4 Hz), 4.69 (2H, s), 2.80 (3H, d, J=5 Hz), 0.93 (9H, s), 0.09 (6H, s). MS m/e 295(M+H)$^+$, 312 (M+NH$_4$)$^+$.

Step 3. Preparation of O-t-butyldimethylsilyl-3-[(N'-N'-dimethylaminocarbonyl)-N-methylamino]benzyl alcohol.

The desired compound was prepared according to the method of Example 5, step 2, except substituting O-t-butyldimethylsilyl-3-[(N'-methylaminocarbonyl)amino] benzyl alcohol, prepared as in step 2, for methyl 4-(N-methylaminocarbonyl)aminobenzoate. $^1$H NMR (300 MHz, CDCl$_3$) δ7.27 (1H, t, J=7.5 Hz), 7.00–7.06 (2H, m), 6.92 (1H, br d, J=7.5 Hz), 4.71 (2H, s), 3.21 (3H, s), 2.68 (6H, s),0.93 (9H, s), 0.09 (6H, s); MS m/e 323 (M+H)$^+$; 340 (M+NH$_4$)$^+$.

Step 4. Preparation of 3-[(N'-N'-dimethylaminocarbonyl)-N-methylamino]benzyl bromide.

To a solution of O-t-butyldimethylsilyl-3-[(N'-N'-methylaminocarbonyl)-N-methylamino]benzyl alcohol (371 mg, 1.15 mmol) in CH$_2$Cl$_2$ (5.7 mL) was added a solution of dibromotriphenylphosphorane (1.45 g, 3.45 mmol) in CH$_2$Cl$_2$ (5.7 mL). The reaction mixture was stirred for stirred for 1.5 hours at ambient temperature and was then partitioned between ethyl acetate and H$_2$O. The organic phase was washed twice with H$_2$O, twice with brine, dried over MgSO$_4$, filtered, and concentrated in vacuo. Pure 3-[(N'-N'-methylaminocarbonyl)-N-methylamino]benzyl bromide (282 mg, 90%) was obtained by chromatography on silica gel. $^1$H NMR (300 MHz, CDCl$_3$) δ7.29 (1H, t, J=7.5 Hz), 7.06–7.12 (2H, m), 6.98 (1H, br d, J=7.5 Hz), 4.46 (2H, s), 3.21 (3H, s), 2.72 (6H, s),0.93 (9H, s), 0.09 (6H, s). MS m/e 271/273 (M+H)$^+$, 288/290 (M+NH$_4$)$^+$.

Step 5. Preparation of E- and Z-O-Methyl-4-[(3-(3-(N',N'-dimethylaminocarbonyl-N-methylamino)benzyloxy)-5-fluoro-phenyl)oximinomethyl]tetrahydropyran.

The desired compound is prepared according to the method of Example 5, step 5, except substituting 3-[(N'-N'-dimethylaminocarbonyl)-N-methylamino]benzyl bromide, prepared as in step 4, for 4-[(N'-N'-dimethylaminocarbonyl)-N-methylamino]benzyl chloride.

EXAMPLE 44

Preparation of E- and Z-O-Methyl-4-[(3-(3-N',N'-dimethylaminocarbonyl-N-methylamino)-benzyloxy)phenyl)oximinomethyl]tetrahydropyran.

The desired compound is prepared according to the method of Example 43, except substituting 4-[(3-hydroxyphenyl)oxomethyl]tetrahydropyran, prepared as in Example 3, step 3, for 4-[(3-hydroxy5-fluorophenyl)oxomethyl]tetrahydropyran.

EXAMPLE 45

Preparation of E- and Z-O-Methyl-4-[(3-(3-(N',N'-dimethylaminocarbonyl-N-methylamino)-benzylthio)-5-fluorophenyl)oximinomethyl]tetrahydropyran.

The desired compound is prepared according to the method of Example 43, except substituting 4-[(3-thioxy-5-fluorophenyl)oxomethyl]tetrahydropyran, prepared as in Example 17, for 4-[(3-hydroxy-5-fluorophenyl)oxomethyl]tetrahydropyran.

EXAMPLE 46

Preparation of E- and Z-O-Methyl-4-[(3-(3-(N',N'-dimethylaminocarbonyl-N-methylamino)-benzylthio)phenyl)oximinomethyl]tetrahydropyran.

The desired compound is prepared according to the method of Example 45, except substituting 4-[(3-thioxyphenyl)oxomethyl]tetrahydropyran, prepared as in Example 13, step 1, for 4-[(3-thioxy-5-fluorophenyl)oxomethyl]tetrahydropyran.

EXAMPLE 47

Preparation of E- and Z-O-Methyl-4-[(3-(3-(N-acetyl-N-methylamino)benzyloxy)-5-fluoro-phenyl)oximinomethyl] tetrahydropyran.

Step 1. Preparation of O-t-butyldimethylsilyl-3-[(N-acetyl))amino]benzyl alcohol.

The desired material is prepared according to the method of Example 1, step 1, except substituting 3-(O-t-butyldimethylsilyloxymethyl)aniline, prepared as in Example 45, step 1, for N-methyl-4-aminobenzoic acid.

Step 2. Preparation of O-t-butyldimethylsilyl-3-[(N-acetyl-N-methyl))amino]benzyl alcohol.

The desired material is prepared according to the method of Example 5, step 2, except substituting O-t-butyldimethylsilyl-3-[(N-acetyl))amino]benzyl alcohol, prepared as in step 1, for methyl 4-(N-methylaminocarbonyl)aminobenzoate.

Step 3. Preparation of E- and Z-O-Methyl-4-[(3-(3-(N-acetyl-N-methylamino)benzyloxy)-5-fluoro-phenyl)oximinomethyl]tetrahydropyran.

The desired compound is prepared according to the method of Example 43, steps 4–5, except substituting O-t-butyldimethylsilyl-3-[(N-acetyl-N-methyl))amino]benzyl alcohol, prepared as in step 2, for O-t-butyldimethylsilyl-3-[(N'-N'-methylaminocarbonyl)-N-methylamino]benzyl alcohol.

EXAMPLE 48

Preparation of E- and Z-O-Methyl-4-[(3-(3-(N-acetyl-N-methylamino)benzyloxy)phenyl)oximinomethyl]tetrahydropyran.

The desired compound is prepared according to the method of Example 47, except substituting 4-[(3-hydroxyphenyl)oxomethyl]tetrahydropyran, prepared as in Example 3, step 3, for 4-[(3-hydroxy-5-fluorophenyl)oxomethyl]tetrahydropyran.

EXAMPLE 49

Preparation of E- and Z-O-Methyl-4-[(3-(3-(N-acetyl-N-methylamino)benzylthio)-5-fluoro-phenyl)oximinomethyl] tetrahydropyran.

The desired compound is prepared according to the method of Example 47, except substituting 4-[(3-thioxy-5-fluorophenyl)oxomethyl]tetrahydropyran, prepared as in Example 17, for 4-[(3-hydroxy-5-fluorophenyl)oxomethyl] tetrahydropyran.

EXAMPLE 50

Preparation of E- and Z-O-Methyl-4-[(3-(3-(N-acetyl-N-methylamino)benzylthio)phenyl)oximinomethyl]tetrahydropyran.

The desired compound is prepared according to the method of Example 49, except substituting 4-[(3-thioxyphenyl)oxomethyl]tetrahydropyran, prepared as in Example 13, step 1, for 4-[(3-thioxy-5-fluorophenyl)oxomethyl]tetrahydropyran.

EXAMPLE 51

Preparation of E- and Z-O-Methyl-4-[(3-(3-(N'N'-dimethylaminocarbonyl-N-methylamino)-benzylamino)phenyl)oximinomethyl]tetrahydropyran.

The desired compound is prepared according to the method of Example 43 except substituting 4-[(3-aminophenyl)oxomethyl]tetrahydropyran, prepared as in Example 9, step 3, for 4-[(3-hydroxy-5-fluorophenyl)oxomethyl]tetrahydropyran.

EXAMPLE 52

Preparation of E- and Z-O-Methyl-4-[(3-(3-(N-acetyl-N-methylamino)benzylamino)phenyl)oximinomethyl]tetrahydropyran.

The desired compound is prepared according to the method of Example 47, except substituting 4-[(3-aminophenyl)oxomethyl]tetrahydropyran, prepared as in Example 9, step 3, for 4-[(3-hydroxy-5-fluorophenyl)oxomethyl]tetrahydropyran.

EXAMPLE 53

Preparation of 4-[(3-(4-(N-acetyl-N-methylamino)benzyloxy)-5-fluoro-phenyl)methoxymethyl]tetrahydropyran.

Step 1. Preparation of 4-[(3-(4-(N-acetyl-N-methylamino)benzyloxy)-5-fluoro-phenyl)hydroxymethyl]tetrahydropyran.

The desired material is prepared by reduction of 4-[(3-(4-(N-acetyl-N-methylamino)benzyloxy)-5-fluoro-phenyl)oxomethyl]tetrahydropyran, prepared as in Example 1, with NaBH$_4$.

Step 2. Preparation of 4-[(3-(4-(N-acetyl-N-methylamino)benzyloxy)-5-fluoro-phenyl)methoxymethyl]tetrahydropyran.

The desired compound is prepared according to the method of Example 5, step 2, except substituting 4-[(3-(4-(N-acetyl-N-methylamino)benzyloxy)-5-fluoro-phenyl)hydroxymethyl]tetrahydropyran, prepared as in step 1, for methyl 4-(N-methylaminocarbonyl)aminobenzoate.

The compounds represented in Table 2 are prepared according to the method of Example 55, except substituting the corresponding ketone for 4-[(3-(4-(N-acetyl-N-methylamino)benzyloxy)-5-fluoro-phenyl)oxomethyl]tetrahydropyran.

TABLE 2

| Example | Product |
| --- | --- |
| 54 |  |
| 55 |  |
| 56 |  |
| 57 |  |

TABLE 2-continued

| Example | Product |
|---|---|
| 58 | (structure) |
| 59 | (structure) |
| 60 | (structure) |
| 61 | (structure) |
| 62 | (structure) |
| 63 | (structure) |

TABLE 2-continued

| Example | Product |
|---|---|
| 64 | |
| 65 | |
| 66 | |
| 67 | |
| 68 | |
| 69 | |
| 70 | |

TABLE 2-continued
| Example | Product |
|---|---|
| 71 | 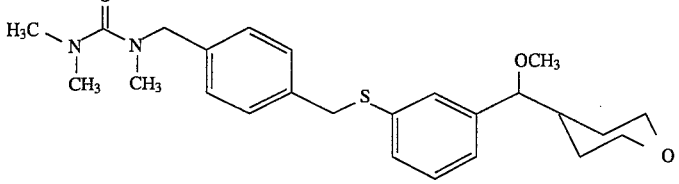 |
| 72 | 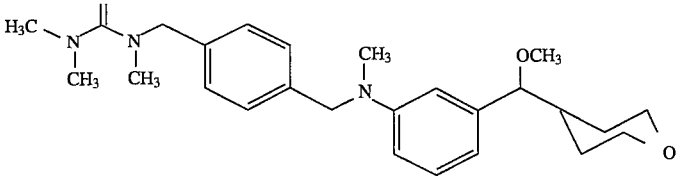 |
| 73 | 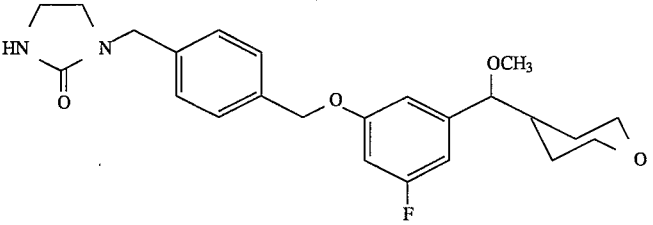 |
| 74 | 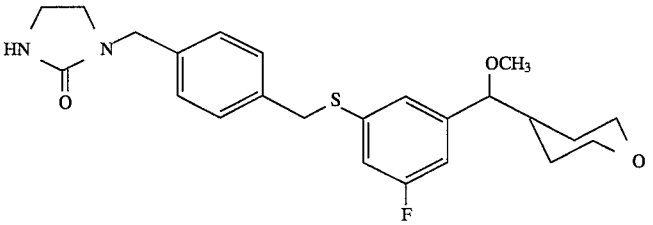 |
| 75 | 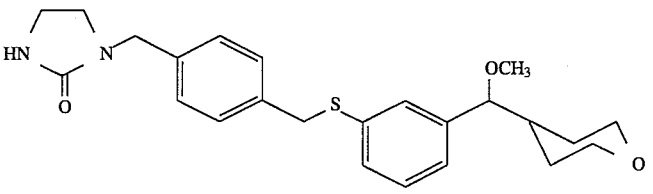 |
| 76 | 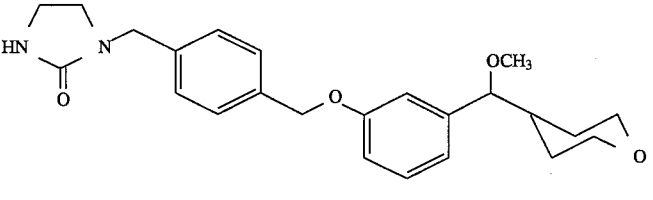 |
| 77 | 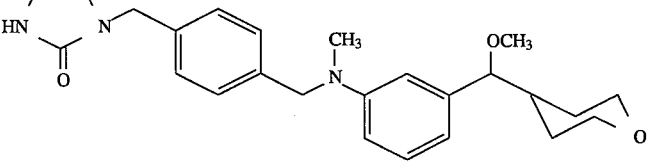 |

TABLE 2-continued

| Example | Product |
|---|---|
| 78 | 3-(N-methylacetamido)benzyl ether: 3-[(methoxy)(tetrahydropyran-4-yl)methyl]-5-fluorophenyl ether |
| 79 | 3-(N-methylacetamido)benzyl thioether: 3-[(methoxy)(tetrahydropyran-4-yl)methyl]-5-fluorophenyl thioether |
| 80 | 3-(N-methylacetamido)benzyl ether: 3-[(methoxy)(tetrahydropyran-4-yl)methyl]phenyl ether |
| 81 | 3-(N-methylacetamido)benzyl thioether: 3-[(methoxy)(tetrahydropyran-4-yl)methyl]phenyl thioether |
| 82 | 3-(N-methylacetamido)benzyl N-methylamine: 3-[(methoxy)(tetrahydropyran-4-yl)methyl]aniline |

TABLE 2-continued

| Example | Product |
|---|---|
| 83 | |
| 84 | |
| 85 | |
| 86 | |
| 87 | |

The compounds represented in Table 3 are prepared by treatment of arylalkylamine 12 with trimethylsilylisocyanate, with $R^7NCO$, or with RLi and $R^6R^7NCOCl$ as described in Scheme 2.

TABLE 3

Novel N-alkylurea inhibitors of 5-lipoxygenase

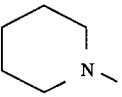

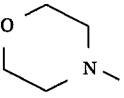

| Example | R⁵ | R⁶ | R⁷ |
|---|---|---|---|
| 88 | Me | H | H |
| 89 | Me | H | Me |
| 90 | Me | H | Et |
| 91 | Me | H | Pr |
| 92 | Me | H | Bu |
| 93 | Me | Et | Me |
| 94 | Me | Pr | Me |
| 95 | Me | Bu | Me |
| 96 | Me | Et | Et |
| 97 | Me | Pr | Pr |
| 98 | Me | Bu | Bu |
| 99 | Me | Ph | H |
| 100 | Me | Ph | Me |
| 101 | Me | 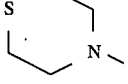 | |
| 102 | Me | 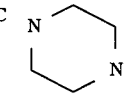 | |
| 103 | Me | 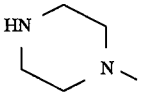 | |
| 104 | Me | 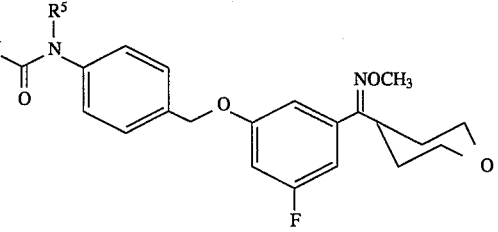 | |
| 105 | Me | 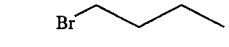 | |
| 106 | Et | H | Me |
| 107 | Et | Me | Me |
| 108 | Pr | H | Me |
| 109 | Pr | Me | Me |
| 110 | Bu | H | Me |
| 111 | Bu | Me | Me |

The compounds represented in Table 4 are prepared by reaction of isocyanate 16 with HNR⁶R⁷.

TABLE 4

Novel haloalkyl-, hydroxyalkyl-, aminoalkyl-, (alkoxycarbonyl)alkyl-, carboxyalkyl-, and (aminoalkylcarbonyl)alkylurea derivatives of 5-Lipoxygenase.

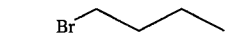

| Example | R⁵ | R⁷ | R⁶ |
|---|---|---|---|
| 112 | Me | 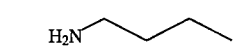 | H |
| 113 | Me | 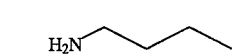 | Me |
| 114 | Me |  | H |
| 115 | Me |  | Me |
| 116 | Me | 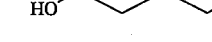 | H |
| 117 | Me |  | Me |
| 118 | Me |  | H |
| 119 | Me |  | Me |
| 120 | Me | 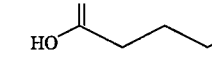 | H |
| 121 | Me | 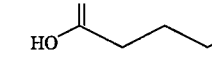 | Me |
| 122 | Me |  | H |
| 123 | Me | 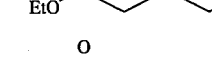 | Me |

The compounds represented in Table 5 are prepared as described in Scheme 6.

TABLE 5

Novel N-acyl inhibitors of 5-Lipoxygenase

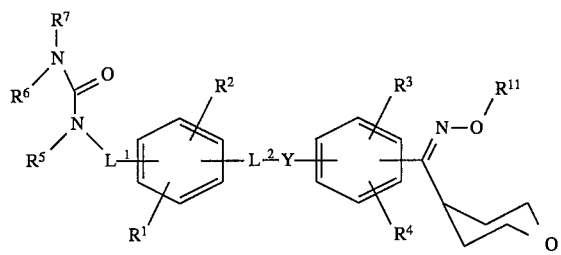

| Example | R⁸ |
|---|---|
| 124 | Br~~~ |
| 125 | NC~~~ |
| 126 | H₂N~~~ |
| 127 | HO~~~ |
| 128 | HOOC~~~ |
| 129 | EtOOC~~~ |
| 130 | CH₃NHC(O)~~~ |

We claim:

1. A compound having the structure

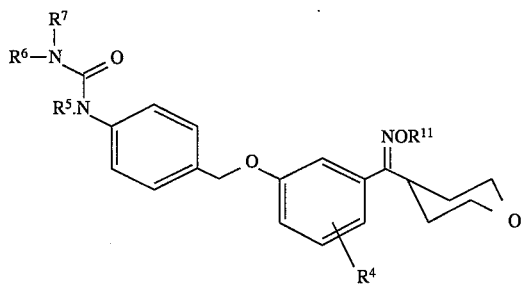

or a pharmaceutically acceptable salt thereof wherein $R^5$ and $R^6$ are independently selected from hydrogen and alkyl of one to four carbon atoms, provided that when $L^1$ is a valence bond, $R^5$ is alkyl of one to four carbon atoms, or $R^5$ and $R^6$, together with the nitrogen atoms to which they are attached, define a radical of the formulae

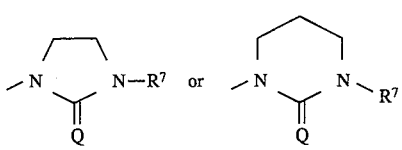

Q is oxygen or sulfur, $R^7$ is selected from the group consisting of hydrogen, and alkyl of one to four carbon atoms;

$L^1$ is a valence bond or is selected from alkylene of one to three carbon atoms, propenylene, and propynylene;

$R^1$, $R^2$, $R^3$, and $R^4$ are independently selected from the group consisting of hydrogen, alkyl of one to four carbon atoms, alkoxy of one to four carbon atoms, haloalkyl, and halogen;

$L^2$ is a valence bond or is selected from alkylene of one to three carbon atoms, propenylene, and propynylene;

Y is oxygen, and $R^{11}$ is hydrogen or alkyl of one to four carbon atoms.

2. A compound as defined in claim 1 having the structure or a pharmaceutically acceptable salt thereof wherein $R^4$, $R^5$, $R^6$, $R^7$, and $R^{11}$ are defined therein.

3. A compound or pharmaceutically acceptable salt thereof selected from the group consisting of:

E and Z-O-Methyl-4-[(3-(4-(N-acetyl-N-methylamino)benzyloxy)-5-fluoro-phenyl)oximinomethyl]tetrahydropyran, E and Z-O-Methyl-4-[(3-(4-(N',N'-dimethylaminocarbonyl-N-methylamino)-benzyloxy)-5-fluorophenyl)oximinomethyl]tetrahydropyran, and E and Z-O-Methyl-4-[(3-(4-(N',N'-dimethylaminocarbonyl-N-methylamino)phenylthio)phenyl)oximinomethyl]tetrahydropyran.

4. A pharmaceutical composition comprising a therapeutically effective amount of a compound as defined in claim 1 in combination with a pharmaceutically acceptable carrier.

5. A method of inhibiting 5-lipoxygenase enzyme activity in a mammal in need of such treatment comprising administering an effective amount of a compound as defined in claim 1.

* * * * *

UNITED STATES PATENT AND TRADEMARK OFFICE
CERTIFICATE OF CORRECTION

PATENT NO. : 5,484,786
DATED : January 16, 1996
INVENTOR(S) : Dellaria, et. Al.

It is certified that error appears in the above-indentified patent and that said Letters Patent is hereby corrected as shown below:

Column 50, line 30, change "$R^5.N$" to --$R^5$-N--.

Signed and Sealed this

Twenty-second Day of July, 1997

Attest:

BRUCE LEHMAN

Attesting Officer          Commissioner of Patents and Trademarks